(12) United States Patent
Malm

(10) Patent No.: US 11,931,398 B2
(45) Date of Patent: Mar. 19, 2024

(54) TERLIPRESSIN COMPOSITIONS AND USES THEREOF

(71) Applicant: Ferring B.V., Hoofddorp (NL)

(72) Inventor: Mattias Malm, Malmö (SE)

(73) Assignee: Ferring B.V., Hoofddorp (NL)

(*) Notice: Subject to any disclaimer, the term of this patent is extended or adjusted under 35 U.S.C. 154(b) by 108 days.

(21) Appl. No.: 17/252,153

(22) PCT Filed: Jun. 14, 2019

(86) PCT No.: PCT/IB2019/055004
§ 371 (c)(1),
(2) Date: Dec. 14, 2020

(87) PCT Pub. No.: WO2019/239386
PCT Pub. Date: Dec. 19, 2019

(65) Prior Publication Data
US 2021/0161995 A1    Jun. 3, 2021

Related U.S. Application Data

(60) Provisional application No. 62/685,447, filed on Jun. 15, 2018.

(51) Int. Cl.
*A61K 38/095* (2019.01)

(52) U.S. Cl.
CPC .................. *A61K 38/095* (2019.01)

(58) Field of Classification Search
CPC .. A61K 38/095; A61K 38/085; A61K 9/0019; C07K 7/14
See application file for complete search history.

(56) References Cited

FOREIGN PATENT DOCUMENTS

| CN | 102068685 A | 5/2011 |
|---|---|---|
| CN | 102440957 A | 5/2012 |
| JP | 09-502424 | 3/1997 |
| WO | WO-2014/176534 A1 | 10/2014 |
| WO | WO-2020/237170 A1 | 11/2020 |

OTHER PUBLICATIONS

"Head of Medical Agencies: Draft Public Assessment Report, scientific discussion," (Sep. 2010) XP055640283, Retrieved from the Internet: URL: http://mri.cts-mrp.eu/download/DK_H_0829_002_PAR.pdf [retrieved on Nov. 7, 2019].
Arora et al., "Terlipressin is superior to Noradrenalie in the management of acute kidney injury (AKI) in patients with ACLF," Journal of Hepatology, vol. 66, No. 1, p. S563 (paragraph SAT-011) (Jun. 2017) XP085012671.
"Variquel Solution, Terlipressin Acetate, Summary of Product Characteristics, Labelling and Package Leaflet," Version 3.1 (Jun. 2015), available at http://mri.cts-mrp.eu/download/NL_H_2566_001_FinalPl.pdf.
The Therapeutic Goods Administration: "Australian Public Assessment Report for terlipressin acetate. Proprietary Product Name: Glypressin. Sponsor: Ferring Pharmaceuticals Pty Ltd," (Nov. 2012) XP055640140, Retrieved from the Internet: URL: https//www.tga.gov.au/sites/default/files/auspar-terlipressin-acetate-121126.pdf [retrieved on Nov. 7, 2019].
Wang et al., "Terlipressin in the treatment of hepatorenal syndrome: A systematic review and meta-analysis," Medicine, vol. 97, No. 16, pp. 1-9 (Apr. 2018) XP055640429.
Office Action received in Chinese Patent Application No. 201980053281.8 dated Apr. 29, 2023.
Meb, "Public Assessment Report of the Medicines Evaluation Board in the Netherlands Glypressin, solution for injection 0.1 mg/ml Ferring B.V., the Netherlands terlipressin acetate," Sep. 21, 2010.
Search Report Received in Taiwanese Patent Application No. 108120774 dated Jul. 12, 2023.
Office Action received in Chinese Patent Application No. 201980053281.8, dated Dec. 7, 2023.

*Primary Examiner* — Sudhakar Katakam

(74) *Attorney, Agent, or Firm* — Foley & Lardner LLP

(57) ABSTRACT

Described herein are pharmaceutical compositions comprising terlipressin and therapeutic methods for using them.

16 Claims, 7 Drawing Sheets

TERLIPRESSIN COMPOSITIONS AND USES THEREOF

RELATED APPLICATIONS

This application is the U.S. National Stage of International Application No. PCT/IB2019/055004, filed Jun. 14, 2019, and claims the priority benefits of U.S. provisional application 62/685,447 filed Jun. 15, 2018, the entire contents of which are incorporated herein by reference.

FIELD

Described herein are stable pharmaceutical compositions comprising terlipressin and therapeutic methods for using them.

BACKGROUND

Cirrhosis is a chronic disorder of the liver where scar tissue replaces the normal liver. When the blood flow to the kidneys becomes insufficient, cirrhosis patients can develop a kidney disease known as hepatorenal syndrome. Terlipressin, a drug that increases the blood flow to the kidneys by constricting blood vessels, has been shown to help people with hepatorenal syndrome.

Terlipressin, also known as triglycyl-lysine vasopressin, is a synthetic peptide. It is an analogue of vasopressin, which is an endogenous vasoactive hormone. Terlipressin has been approved in many countries outside of the United States for the treatment of life-threatening complications of cirrhosis, including hepatorenal syndrome (HRS) and esophageal bleeding (EVB). The structural formula of terlipressin is as follows:

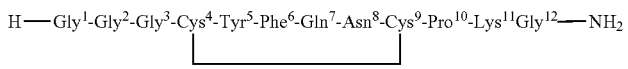

which also can be represented as follows:

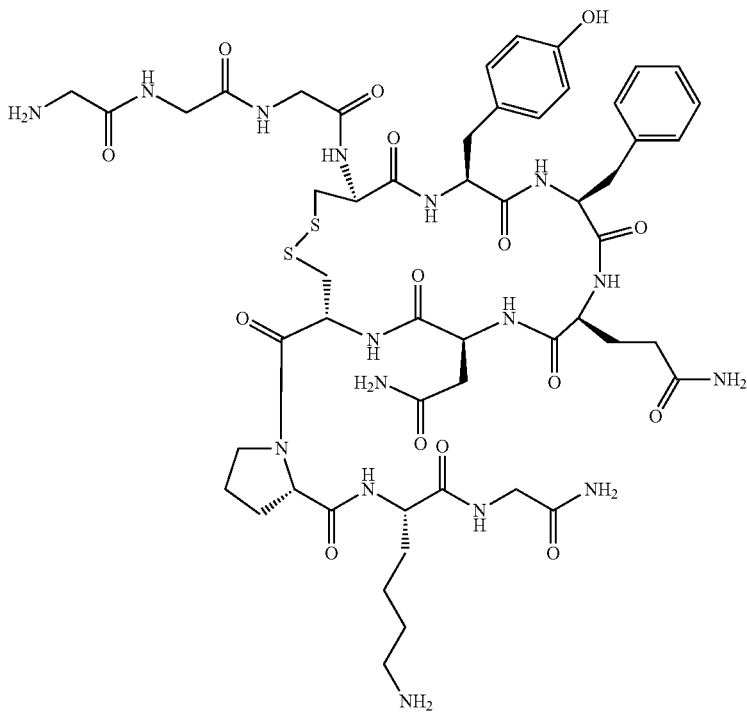 [SMILES: NCCCC[C@H](NC(=O)[C@@H]1CCCN1C(=O)[C@@H]1CSSC[C@@H](NC(=O)CNC(=O)CNC(=O)CN)C(=O)N[C@@H](Cc2ccc(O)cc2)C(=O)N[C@@H](Cc2ccccc2)C(=O)N[C@@H](CCC(N)=O)C(=O)N[C@@H](CC(N)=O)C(=O)N1)C(=O)NCC(N)=O]

Due to terlipressin's short half-life, its use has been limited in the hospital setting. GLYPRESSIN® 0.1 mg/mL is the current Ferring liquid formulation of terlipressin. The product is available as a solution for injection in a 10 mL glass ampoule type I with a fill volume of 8.5 mL. The product contains 0.1 mg/mL of terlipressin free base (corresponding to approximately 0.12 mg/mL as acetate salt), 20 mM of acetate buffer and 9 mg/mL of NaCl. The pH of the product is pH 3.5-4.5 with a pH adjusted between 3.6-3.9. This product must be stored in a refrigerator and has a shelf-life of 24 months at 2-8° C. To improve the usability of the product outside hospitals, e.g. in ambulances, it would be desirable to develop a liquid terlipressin formulation with improved shelf-life that is stable at room temperature (about 25° C. or about 30° C.) for at least 1 or 2 years.

SUMMARY

In one aspect, provided herein are pharmaceutical compositions comprising terlipressin or a pharmaceutically acceptable salt thereof, a monovalent organic buffer salt in an amount that provides a total buffer concentration in the composition of 5 mM or less, optionally, an isotonic agent, and water. The composition may have a pH of from about 4.5 to about 6. In some embodiments, the composition has a pH of from about 4.5 to about 5.5.

In some embodiments, the isotonic agent is or comprises mannitol. In some embodiments, the isotonic agent is or comprises a salt selected from one or more of potassium sulfate ($K_2SO_4$), ammonium sulfate (($NH_4$)$_2SO_4$), sodium sulfate ($Na_2SO_4$), magnesium sulfate ($MgSO_4$), sodium chloride (NaCl), and sodium iodide (NaI). In some embodiments, the isotonic agent comprises sodium chloride, such as at a concentration ranging from about 1 mg/mL to about 10 mg/mL. In some embodiments, the isotonic agent comprises mannitol, such as at a concentration ranging from about 30 mg/mL to about 70 mg/mL.

In some embodiments, the buffer salt is one or more selected from an acetate buffer salt and a benzoate buffer salt. In some embodiments, acetate buffer salt is selected from one or more of sodium acetate, ammonium acetate, and potassium acetate. In some embodiments, the acetate buffer salt is sodium acetate. In some embodiments, the buffer salt is present in an amount to provide a total buffer concentration ranging from about 0.1 mM to about 5 mM.

In some embodiments, the pharmaceutical composition comprises terlipressin or pharmaceutically acceptable salt thereof in an amount to provide from about 0.1 mg/mL to about 5 mg/mL terlipressin free base. In some embodiments, the pharmaceutical composition comprises terlipressin acetate in an amount to provide from about 0.1 mg/mL to about 5 mg/mL terlipressin free base.

In some embodiments, the pharmaceutical composition comprises or consists essentially of terlipressin acetate in an amount to provide from about 0.1 mg/mL to about 5 mg/mL terlipressin free base, sodium acetate in an amount to provide a total acetate concentration ranging from about 0.1 mM to about 5 mM, optionally, sodium chloride at a concentration ranging from about 1 mg/mL to about 10 mg/mL, and water.

In some embodiments, the pharmaceutical composition comprises terlipressin acetate in an amount to provide 0.1 mg/mL terlipressin free base, sodium acetate in an amount to provide a total acetate concentration of about 1 mM, sodium chloride at a concentration of about 9 mg/mL, and water, wherein the composition has a pH of about 4.8±0.3. In some embodiments, the pharmaceutical composition comprises terlipressin acetate in an amount to provide 1 mg/mL terlipressin free base, sodium acetate in an amount to provide a total acetate concentration of about 1 mM, sodium chloride at a concentration of about 9 mg/mL, and water, wherein the composition has a pH of about 4.8±0.3. In some embodiments, the pharmaceutical composition comprises terlipressin acetate in an amount to provide 2 mg/mL terlipressin free base, sodium acetate in an amount to provide a total acetate concentration of about 1 mM, sodium chloride at a concentration of about 9 mg/mL, and water, wherein the composition has a pH of about 4.8±0.3. In some embodiments, the pharmaceutical composition comprises terlipressin acetate in an amount to provide 3 mg/mL terlipressin free base, sodium acetate in an amount to provide a total acetate concentration of about 1 mM, sodium chloride at a concentration of about 9 mg/mL, and water, wherein the composition has a pH of about 4.8±0.3. In some embodiments, the pharmaceutical composition comprises terlipressin acetate in an amount to provide 4 mg/mL terlipressin free base, sodium acetate in an amount to provide a total acetate concentration of about 1 mM, sodium chloride at a concentration of about 9 mg/mL, and water, wherein the composition has a pH of about 4.8±0.3. In some embodiments, the pharmaceutical composition comprises terlipressin acetate in an amount to provide 5 mg/mL terlipressin free base, sodium acetate in an amount to provide a total acetate concentration of about 1 mM, sodium chloride at a concentration of about 9 mg/mL, and water, wherein the composition has a pH of about 4.8±0.3.

In some embodiments, the pharmaceutical composition comprises terlipressin acetate in an amount to provide 0.1 mg/mL terlipressin free base, sodium acetate in an amount to provide a total acetate concentration of about 1 mM, and water, wherein the composition has a pH of about 4.8±0.3. In some embodiments, the pharmaceutical composition comprises terlipressin acetate in an amount to provide 1 mg/mL terlipressin free base, sodium acetate in an amount to provide a total acetate concentration of about 1 mM, and water, wherein the composition has a pH of about 4.8±0.3. In some embodiments, the pharmaceutical composition comprises terlipressin acetate in an amount to provide 2 mg/mL terlipressin free base, sodium acetate in an amount to provide a total acetate concentration of about 1 mM, and water, wherein the composition has a pH of about 4.8±0.3. In some embodiments, the pharmaceutical composition comprises terlipressin acetate in an amount to provide 3 mg/mL terlipressin free base, sodium acetate in an amount to provide a total acetate concentration of about 1 mM, and water, wherein the composition has a pH of about 4.8±0.3. In some embodiments, the pharmaceutical composition comprises terlipressin acetate in an amount to provide 4 mg/mL terlipressin free base, sodium acetate in an amount to provide a total acetate concentration of about 1 mM, and water, wherein the composition has a pH of about 4.8±0.3. In some embodiments, the pharmaceutical composition comprises terlipressin acetate in an amount to provide 5 mg/mL terlipressin free base, sodium acetate in an amount to provide a total acetate concentration of about 1 mM, and water, wherein the composition has a pH of about 4.8±0.3.

In accordance with any embodiments, the pharmaceutical composition may be stable at room temperature for at least 1 year. In some embodiments, after being stored at 25° C. and 60% relative humidity for a period of time of at least one year, the total impurity content in the composition is less than about 1.9% w/w based on the total weight of the terlipressin. In some embodiments, the period of time is selected from one year, 18 months, 24 months, and 36 months. In some embodiments, the period of time is 12 months.

In another aspect, provided herein are methods of treatment comprising administering any one of the pharmaceutical terlipressin compositions described herein to a subject in need thereof. In some embodiments, the method is for treating esophageal bleeding (EVB). In some embodiments, the method is for treating hepatorenal syndrome (HRS). In some embodiments, the method is for treating acute kidney injury. In some embodiments, the administering is by intravenous injection.

In another aspect, provided herein are pharmaceutical terlipressin compositions described herein for use in treating a condition selected from esophageal bleeding (EVB), hepatorenal syndrome, and acute kidney injury.

In another aspect, provided herein are uses of terlipressin or a pharmaceutically acceptable salt thereof in the preparation of a medicament for treating esophageal bleeding (EVB), hepatorenal syndrome, or acute kidney injury, wherein the medicament comprises any one of the pharmaceutical terlipressin compositions described herein.

In another aspect, provided herein are pharmaceutical compositions comprising terlipressin or a pharmaceutically acceptable salt thereof, at least one a buffer salt, and at least one a salt selected from one or more of chosen from potassium sulfate ($K_2SO_4$), ammonium sulfate (($NH_4$)$_2SO_4$), sodium sulfate ($Na_2SO_4$), magnesium sulfate ($MgSO_4$), sodium chloride (NaCl), and sodium iodide (NaI).

DETAILED DESCRIPTION

Figure 1:
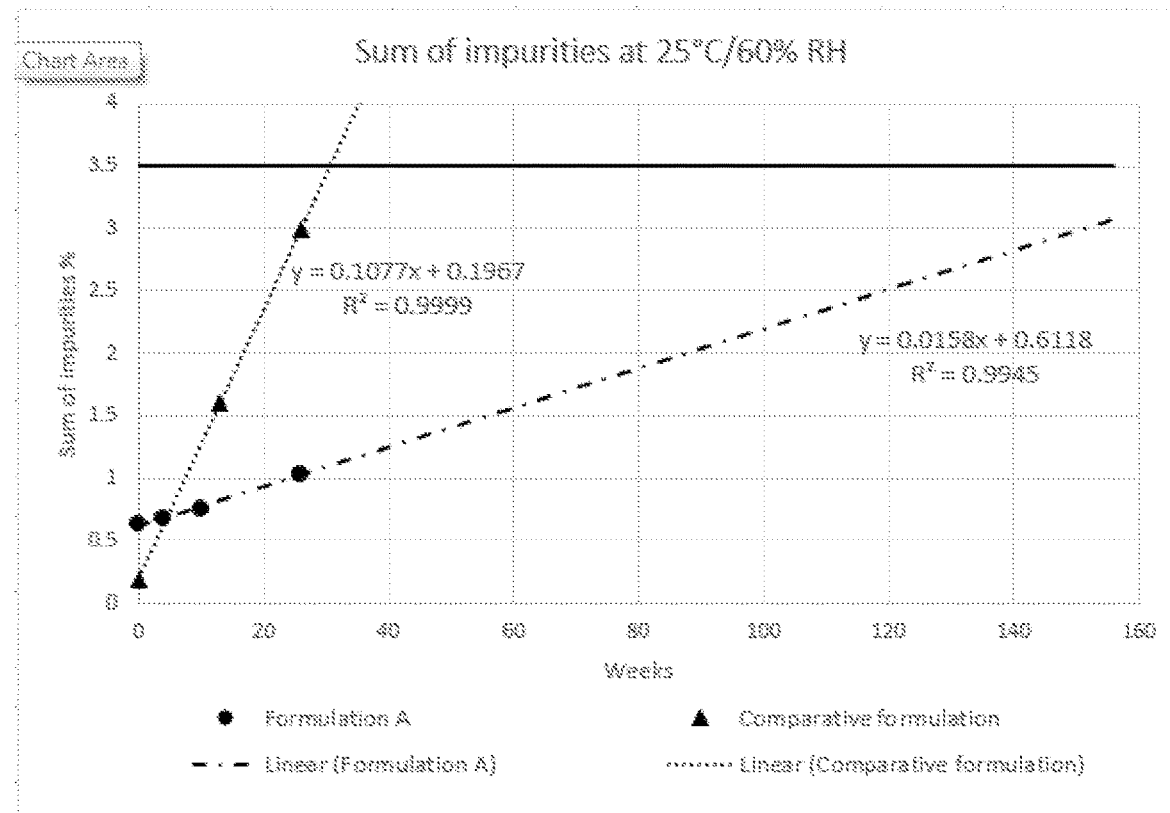
FIG. 1 is a graphical depiction of the sum of impurities for Formulation A and a Comparative Formula under storage at 25° C. for 26 weeks.

The present disclosure provides pharmaceutically acceptable terlipressin compositions comprising terlipressin or a pharmaceutically acceptable salt thereof, a buffer salt, such as a monovalent organic buffer salt (e.g., an acetate buffer salt or a benzoate buffer salt), optionally, an isotonic agent, such as mannitol or a salt selected from one or more of potassium sulfate ($K_2SO_4$), ammonium sulfate (($NH_4$)$_2SO_4$), sodium sulfate ($Na_2SO_4$), magnesium sulfate ($MgSO_4$), sodium chloride (NaCl), and sodium iodide (NaI), and water. The compositions may have a total buffer concentration of 5 mM or less, such as from 0.1 mM to about 5 mM.

The compositions described herein exhibit good stability against the formation of impurities. In some embodiments, the compositions are stable at room temperature for at least one year. In some embodiments, the compositions described herein have improved stability as compared to the commercial formulation GLYPRESSIN®, such as may be reflected in reduced formation of impurities. Without being bound by any theory, the improved stability of the compositions described herein is attributed to the specific combination of ingredients and amounts thereof, as well as the pH.

Definitions

Technical and scientific terms used herein have the meanings commonly understood by one of ordinary skill in the art of pharmaceutical formulations to which the present disclosure pertains, unless otherwise defined. Reference is made herein to various methodologies known to those of ordinary skill in the art. Suitable materials and/or methods known to those of ordinary skill in the art can be utilized in carrying out the present disclosure. However, specific materials and methods are described. Materials, reagents and the like to which reference is made in the following description and examples are obtainable from commercial sources, unless otherwise noted.

As used herein, the singular forms "a," "an," and "the" designate both the singular and the plural, unless expressly stated to designate the singular only.

As used herein, the term "about" means that the number or range is not limited to the exact number or range set forth, but encompass values around the recited number or range as will be understood by persons of ordinary skill in the art depending on the context in which the number or range is used. Unless otherwise apparent from the context or convention in the art, "about" means up to plus or minus 10% of the particular term.

The term "pharmaceutically acceptable salt" as used herein, refers to pharmaceutically acceptable organic or inorganic salts of the referenced compound. Exemplary salts include, but are not limited, to sulfate, citrate, acetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucuronate, saccharate, formate, benzoate, glutamate, methanesulfonate "mesylate," ethanesulfonate, benzenesulfonate, p-toluenesulfonate, pamoate (i.e., 1,1'-methylene-bis-(2-hydroxy-3-naphthoate)) salts, alkali metal (e.g., sodium and potassium) salts, alkaline earth metal (e.g., magnesium) salts, and ammonium salts. In some embodiments, the pharmaceutically acceptable salt of terlipressin is the acetate salt.

As used herein, "subject" denotes any mammal, including humans. For example, a subject may be suffering from or at risk of developing a condition that can be diagnosed, treated or prevented with terlipressin, or may be taking terlipressin for other purposes.

The terms "administer," "administration," or "administering" as used herein refer to providing, giving, dosing and/or prescribing, such as by either a health professional or his or her authorized agent or under his direction, and putting into, taking or consuming, such as by a health professional or the subject.

The terms "treat", "treating" or "treatment", as used herein, include alleviating, abating or ameliorating a disease or condition or one or more symptoms thereof, whether or not the disease or condition is considered to be "cured" or "healed" and whether or not all symptoms are resolved. The terms also include reducing or preventing progression of a disease or condition or one or more symptoms thereof, impeding or preventing an underlying mechanism of a disease or condition or one or more symptoms thereof, and achieving any therapeutic and/or prophylactic benefit.

As used herein, the phrase "therapeutically effective amount" refers to a dose that provides the specific pharmacological effect for which the drug is administered in a subject in need of such treatment. It is emphasized that a therapeutically effective amount will not always be effective in treating the conditions described herein, even though such dose is deemed to be a therapeutically effective amount by those of skill in the art. For convenience only, exemplary doses and therapeutically effective amounts are provided below with reference to adult human subjects. Those skilled in the art can adjust such amounts in accordance with standard practices as needed to treat a specific subject and/or condition/disease.

The terms "comprising," "including," "containing," etc., shall be read expansively and without limitation. Additionally, the phrase "consisting essentially of" will be understood to include those elements specifically recited and additional elements that do not materially affect the basic and novel characteristics of the claimed invention, such as ingredients that do not materially impact the stability of the composition or promote the formation of impurities. For example, "consisting essentially of" excludes the presence of citrate or succinate buffers in an amount that materially impacts the stability of the composition. The phrase "consisting of" excludes any element not specified.

Terlipressin

As noted above, the compositions described herein include terlipressin or a pharmaceutically acceptable salt thereof, such as the acetate salt. Terlipressin is also known as N—[N—(N-Glycylglycyl)glycyl]-8-L-lysinevasopressin, and has the molecular formula $C_{52}H_{74}N_{16}O_{15}S_2$ and a molecular weight of 1227.4. It is registered under CAS Registry Number 14636-12-5.

The compositions may comprise terlipressin or pharmaceutically acceptable salt thereof in an amount to provide from about 0.01 mg/mL to about 10 mg/mL terlipressin free base, including from about 0.1 mg/mL to about 5 mg/mL terlipressin free base, such as from 0.1 mg/mL to 5 mg/mL, such as about 0.01 mg/mL, about 0.05 mg/mL, about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, about 1.0 mg/mL, about 2.0 mg/mL, about 3.0 mg/mL, about 4.0 mg/mL, about 5 mg/mL, about 6 mg/mL, about 7 mg/mL, about 8 mg/mL, about 9 mg/mL, or about 10 mg/mL, including 0.01 mg/mL, 0.05 mg/mL, 0.1 mg/mL, 0.2 mg/mL, 0.3 mg/mL, 0.4 mg/mL, 0.5 mg/mL, 0.6 mg/mL, 0.7 mg/mL, 0.8 mg/mL, 0.9 mg/mL, 1.0 mg/mL, 2.0 mg/mL, 3.0 mg/mL, 4.0 mg/mL, 5 mg/mL, 6 mg/mL, 7 mg/mL, 8 mg/mL, 9 mg/mL, or 10 mg/mL. The compositions may comprise terlipressin or pharmaceutically acceptable salt thereof in an amount to provide about 0.1 mg/mL terlipressin free base, including in an amount to provide 0.1 mg/mL terlipressin free base, In some embodiments, the composition comprises terlipressin acetate in an amount to provide from about 0.01 mg/mL to about 10 mg/mL terlipressin free base, including from about 0.1 mg/mL to about 5 mg/mL terlipressin free base, such as from 0.1 mg/mL to 5mg/mL, such as about 0.01 mg/mL, about 0.05 mg/mL, about 0.1 mg/mL, about 0.2 mg/mL, about 0.3 mg/mL, about 0.4 mg/mL, about 0.5 mg/mL, about 0.6 mg/mL, about 0.7 mg/mL, about 0.8 mg/mL, about 0.9 mg/mL, about 1.0 mg/mL, about 2.0 mg/mL, about 3.0 mg/mL, about 4.0 mg/mL, about 5 mg/mL, about 6 mg/mL, about 7 mg/mL, about 8 mg/mL, about 9 mg/mL, or about 10 mg/mL, including 0.01 mg/mL, 0.05 mg/mL, 0.1 mg/mL, 0.2 mg/mL, 0.3 mg/mL, 0.4 mg/mL, 0.5 mg/mL, 0.6 mg/mL, 0.7 mg/mL, 0.8 mg/mL, 0.9 mg/mL, 1.0 mg/mL, 2.0 mg/mL, 3.0 mg/mL, 4.0 mg/mL, 5 mg/mL, 6 mg/mL, 7 mg/mL, 8 mg/mL, 9 mg/mL, or 10 mg/mL. In some embodiments, the composition comprises terlipressin acetate in an amount to provide about 0.1 mg/mL terlipressin free base, including in an amount to provide 0.1 mg/mL terlipressin free base. In some embodiments, the composition comprises terlipressin acetate in an amount to provide about 1 mg/mL terlipressin free base, including in an amount to provide 1 mg/mL terlipressin free base. In some embodiments, the composition comprises terlipressin acetate in an amount to provide about 2 mg/mL terlipressin free base, including in an amount to provide 2 mg/mL terlipressin free base. In some embodiments, the composition comprises terlipressin acetate in an amount to provide about 3 mg/mL terlipressin free base, including in an amount to provide 3 mg/mL terlipressin free base. In some embodiments, the composition comprises terlipressin acetate in an amount to provide about 4 mg/mL terlipressin free base, including in an amount to provide 4 mg/mL terlipressin free base. In some embodiments, the composition comprises terlipressin acetate in an amount to provide about 5 mg/mL terlipressin free base, including in an amount to provide 5 mg/mL terlipressin free base.

pH

In some embodiments, the pharmaceutically acceptable terlipressin compositions have a pH ranging from about 3 to about 6, such as at a pH of about 3, about 3.5, about 3.7, about 4, about 4.3, about 4.5, about 4.7, about 5, about 5.5, or about 6. The compositions described herein may have a pH ranging from about 4.5 to about 6, or from about 4.5 to about 5, including a pH of from 4.5 to 6, or a pH of from 4.5 to 5, such as a pH of about 4.5, about 4.6, about 4.7, about 4.8, about 4.9, about 5.0, about 5.1, about 5.2 about 5.3, about 5.4, about 5.5, about 5.6, about 5.5, about 5.7, about 5.8, about 5.9, or about 6.0, or any value therebetween. Non-limiting examples also include a pH of 4.5, 4.6, 4.7, 4.8, 4.9, 5.0, 5.1, 5.2 5.3, 5.4, 5.5, 5.6, 5.5, 5.7, 5.8, 5.9, or 6.0. The pharmaceutically acceptable terlipressin compositions may have a pH ranging from about 4.5 to about 5, such as at a pH of about 4.5, about 4.6, about 4.7, about 4.8, about 4.9, or about 5.0. Non-limiting examples also include a pH of 4.5, 4.6, 4.7, 4.8, 4.9, or 5.0.

Buffer Salt

As noted above, the compositions described herein comprise a buffer salt, such as a pharmaceutically acceptable monovalent organic buffer salt (e.g., an acetate buffer salt or a benzoate buffer salt). The buffer salt may be present in an amount to provide a total buffer concentration in the composition ranging from about 0.1 mM to about 5 mM, including any value therebetween, such as from about 0.1 mM to about 1 mM. In compositions comprising terlipressin acetate, the terlipressin acetate will contribute to the buffer concentration. For example, 0.12 mg/mL terlipressin acetate corresponds to 0.2 mM acetate. Thus, for example, in a composition comprising 0.12 mg/mL terlipressin acetate (corresponding to 0.10 mg/mL terlipressin free base), the terlipressin acetate will provide 0.2 mM acetate buffer, in a composition comprising 1.2 mg/mL terlipressin acetate (corresponding to 1.0 mg/mL terlipressin free base) the terlipressin acetate will provide 2 mM acetate buffer, in a composition comprising 2.4 mg/mL terlipressin acetate (corresponding to 2.0 mg/mL terlipressin free base) the terlipressin acetate will provide 4 mM acetate buffer, etc. Accordingly, in compositions comprising terlipressin acetate, the amount of buffer salt used may be adjusted to take into account the acetate provided by the terlipressin acetate, such that the total buffer concentration in the composition (from the buffer salt and terlipressin acetate) is any of the amounts described herein.

In some embodiments, the buffer salt comprises acetate, such as may be provided by any pharmaceutically acceptable acetate salt. Such a composition may comprise an acetate buffer salt in an amount to provide a total acetate concentration in the composition ranging from about 0.1 mM to about 5 mM, including any value therebetween, such as from about 0.1 mM to about 1 mM, including from 0.1 mM to 1 mM. As a non-limiting example, the composition may comprise an acetate buffer salt at a concentration of about 1 mM, about 3 mM, or about 5 mM, or in an amount to provide a total acetate concentration in the composition of about 1 mM, about 3 mM, or about 5 mM. The composition may comprise an acetate buffer salt at a concentration ranging from, or in an amount to provide a total acetate concentration in the composition of, about 0.1 mM to about 1 mM, including any value therebetween, such as about 0.1 mM, about 0.2 mM, about 0.3 mM, about 0.4 mM, about 0.5 mM, about 0.6 mM, about 0.7 mM, about 0.8 mM, about 0.9 mM, or about 1.0 mM, about 1.1 mM, or about 1.2 mM. Non-limiting examples of suitable acetate concentrations also include 0.1 mM, 0.2 mM, 0.3 mM, 0.4 mM, 0.5 mM, 0.6 mM, 0.7 mM, 0.8 mM, 0.9 mM, 1.0 mM, 1.1 mM, or 1.2 mM. As noted above, compositions comprising 0.12 mg/mL terlipressin acetate will have an acetate buffer concentration of 0.2 mM even without adding additional acetate buffer salt (etc.).

In some embodiments, the acetate buffer salt is sodium acetate, ammonium acetate, or potassium acetate. Thus, the buffer salt may be sodium acetate. Additionally or alternatively, the buffer salt may be ammonium acetate. Additionally or alternatively, the buffer salt may be potassium acetate.

In some embodiments, the at least one buffer salt comprises benzoate, such as may be provided by any pharmaceutically accepted benzoate salt. Such a composition may comprise a benzoate buffer salt at concentration ranging from, or in an amount to provide a total buffer concentration in the composition of, about 0.1 mM to about 5 mM, including any value therebetween, such as from about 0.1 mM to about 1 mM, including from 0.1 mM to 1 mM. As a non-limiting example, the composition may comprise a benzoate buffer salt at a concentration of, or in an amount to provide a total buffer concentration in the composition of, about 1 mM. The composition may comprise a benzoate buffer salt at a concentration ranging from, or in an amount to provide a total buffer concentration in the composition of, about 0.1 mM to about 1 mM, including any value therebetween, such as about 0.1 mM, about 0.2 mM, about 0.3 mM, about 0.4 mM, about 0.5 mM, about 0.6 mM, about 0.7 mM, about 0.8 mM, about 0.9 mM, or about 1.0 mM, about 1.1 mM, or about 1.2 mM. Non-limiting examples of suitable benzoate buffer salt concentrations, or total buffer concentrations in the composition, also include 0.1 mM, 0.2 mM, 0.3 mM, 0.4 mM, 0.5 mM, 0.6 mM, 0.7 mM, 0.8 mM, 0.9 mM, 1.0 mM, 1.1 mM, or 1.2 mM.

In some embodiments, the at least one buffer salt is sodium benzoate. In some embodiments, the composition comprises sodium benzoate at a concentration of, or in an amount to provide a total buffer concentration in the composition of, about 1 mM.

In compositions comprising terlipressin acetate, the amount of benzoate buffer salt used may be adjusted to take into account the acetate provided by the terlipressin acetate, such that the total buffer concentration in the composition (benzoate plus acetate) is any of the amounts set forth above, such as having a total acetate plus benzoate concentration of about 1 mM.

Isotonic Agent/Salts

As noted above, in some embodiments, the compositions described herein comprise an isotonic agent, such as a salt selected from one or more of potassium sulfate ($K_2SO_4$), ammonium sulfate (($NH_4)_2SO_4$), sodium sulfate ($Na_2SO_4$), magnesium sulfate ($MgSO_4$), sodium chloride (NaCl), and sodium iodide (NaI), or mannitol. The isotonic agent may be present in any amount effective to make the composition isotonic.

In some embodiments, the isotonic agent is the salt sodium chloride. The sodium chloride may be present in an amount effective to make the composition isotonic. Thus, the composition may comprise sodium chloride at a concentration ranging from about 1 mg/mL to about 10 mL/mL, including any amount therebetween, such as about 1 mg/mL, about 1.5 mg/mL, about 2.0 mg/mL, about 2.5 mg/mL, about 3.0 mg/mL, about 3.5 mg/mL, about 4.0 mg/mL, about 4.5 mg/mL, about 5.0 mg/mL, about 5.5 mg/mL, about 6.0 mg/mL, about 6.5 mg/mL, about 7.0 mg/mL, about 7.5 mg/mL, about 8.0 mg/mL, about 8.5 mg/mL, about 9.0 mg/mL, about 9.5 mg/mL, or about 10.0 mg/mL. Non-limiting examples of suitable sodium chloride concentrations also include 1 mg/mL, 1.5 mg/mL, 2.0 mg/mL, 2.5 mg/mL, 3.0 mg/mL, 3.5 mg/mL, 4.0 mg/mL, 4.5 mg/mL, 5.0 mg/mL, 5.5 mg/mL, 6.0 mg/mL, 6.5 mg/mL, 7.0 mg/mL, 7.5 mg/mL, 8.0 mg/mL, 8.5 mg/mL, 9.0 mg/mL, 9.5 mg/mL, or 10.0 mg/mL.

In some embodiments, the isotonic agent is mannitol. The mannitol may be present in any amount effective to make the composition isotonic. Thus, the composition may comprise mannitol at a concentration ranging from about 30 mg/mL to about 70 mL/mL, including any amount therebetween, such as about 30 mg/mL, about 35 mg/mL, about 40 mg/mL, about 45 mg/mL, about 50 mg/mL, about 55 mg/mL, about 60 mg/mL, about 65mg/mL, or about 70 mg/mL. Non-limiting examples of suitable mannitol concentrations also include 30 mg/mL, 35 mg/mL, 40 mg/mL, 45 mg/mL, 50 mg/mL, 55 mg/mL, 60 mg/mL, 65mg/mL, or 70 mg/mL. In specific embodiments, the composition includes mannitol at a concentration of about 50 mg/mL, such as 50 mg/mL.

In some embodiments, the composition includes the salt sodium sulfate. Further in some embodiments, the composition comprises sodium sulfate at a concentration ranging from about 0.1 mM to about 120 mM. In some embodiments, the composition comprises sodium sulfate at a concentration of about 120 mM. In some embodiments, the composition does not include sodium sulfate.

Compositions

The present disclosure includes terlipressin compositions comprising any amount of terlipressin or a pharmaceutically acceptable salt thereof, any amount of any buffer salt(s) described above, and, optionally, any amount of isotonic agent(s) (e.g., salt(s) and/or mannitol) described above, at any suitable pH described above. The present disclosure also includes terlipressin compositions comprising any amount of terlipressin or a pharmaceutically acceptable salt thereof, any amount of any pharmaceutically acceptable monovalent organic buffer salt(s) described above that provides a total buffer concentration in the composition of from about 0.1 mM to about 5 mM, and, optionally, any amount of isotonic agent(s) described above, at any suitable pH described above. The following are disclosed as specific illustrative embodiments.

In some embodiments, the composition comprises terlipressin acetate in an amount to provide from about 0.1 mg/mL to about 5 mg/mL terlipressin free base, an acetate buffer salt in an amount to provide a total acetate concentration ranging from about 0.1 mM to about 5 mM, optionally, sodium chloride at a concentration ranging from about 1 mg/mL to about 10 mg/mL, and water, and has a pH of from 4.5 to about 5.5.

In some embodiments, the composition consists essentially of terlipressin acetate in an amount to provide from about 0.1 mg/mL to about 5 mg/mL terlipressin free base, an acetate buffer salt in an amount to provide a total acetate concentration ranging from about 0.1 mM to about 5 mM, optionally, sodium chloride at a concentration ranging from about 1 mg/mL to about 10 mg/mL, and water. Such a composition does not include any additional ingredients that may materially impact the stability of the composition or promote the formation of impurities. In some embodiments, such a composition does not include a citrate buffer salt and does not include a succinate buffer salt. Additionally or alternatively, in some embodiments such a composition does not include a sulfate salt (such as sodium sulfate).

In some embodiments, the composition comprises terlipressin acetate in an amount to provide 0.1 mg/mL terlipressin free base, sodium acetate in an amount to provide a total acetate concentration of about 1 mM sodium chloride at a concentration of about 9 mg/mL, and water. Such a composition may have a pH of 4.8±0.3.

In some embodiments, the composition comprises terlipressin acetate in an amount to provide 1 mg/mL terlipressin free base, sodium acetate in an amount to provide a total acetate concentration of about 1 mM, sodium chloride at a concentration of about 9 mg/mL, and water. Such a composition may have a pH of 4.8±0.3.

In some embodiments, the composition comprises terlipressin acetate in an amount to provide 2 mg/mL terlipressin free base, sodium acetate in an amount to provide a total acetate concentration of about 1 mM, sodium chloride at a concentration of about 9 mg/mL, and water. Such a composition may have a pH of 4.8±0.3.

In some embodiments, the composition comprises terlipressin acetate in an amount to provide 3 mg/mL terlipressin free base, sodium acetate in an amount to provide a total acetate concentration of about 1 mM, sodium chloride at a concentration of about 9 mg/mL, and water. Such a composition may have a pH of 4.8±0.3.

In some embodiments, the composition comprises terlipressin acetate in an amount to provide 4 mg/mL terlipressin free base, sodium acetate in an amount to provide a total acetate concentration of about 1 mM, sodium chloride at a concentration of about 9 mg/mL, and water. Such a composition may have a pH of 4.8±0.3.

In some embodiments, the composition comprises terlipressin acetate in an amount to provide 5 mg/mL terlipressin free base, sodium acetate in an amount to provide a total acetate concentration of about 1 mM, sodium chloride at a concentration of about 9 mg/mL, and water. Such a composition may have a pH of 4.8±0.3.

In some embodiments, the composition comprises terlipressin acetate in an amount to provide 0.1 mg/mL terlipressin free base, sodium acetate in an amount to provide a total acetate concentration of about 1 mM, and water. Such a composition may have a pH of 4.8±0.3.

In some embodiments, the composition comprises terlipressin acetate in an amount to provide 1 mg/mL terlipressin free base, sodium acetate in an amount to provide a total acetate concentration of about 1 mM, and water. Such a composition may have a pH of 4.8±0.3.

In some embodiments, the composition comprises terlipressin acetate in an amount to provide 2 mg/mL terlipressin free base, sodium acetate in an amount to provide a total acetate concentration of about 1 mM, and water. Such a composition may have a pH of 4.8±0.3.

In some embodiments, the composition comprises terlipressin acetate in an amount to provide 3 mg/mL terlipressin free base, sodium acetate in an amount to provide a total acetate concentration of about 1 mM, and water. Such a composition may have a pH of 4.8±0.3.

In some embodiments, the composition comprises terlipressin acetate in an amount to provide 4 mg/mL terlipressin free base, sodium acetate in an amount to provide a total acetate concentration of about 1 mM, and water. Such a composition may have a pH of 4.8±0.3.

In some embodiments, the composition comprises terlipressin acetate in an amount to provide 5 mg/mL terlipressin free base, sodium acetate in an amount to provide a total acetate concentration of about 1 mM, and water. Such a composition may have a pH of 4.8±0.3.

In some embodiments, the pharmaceutically acceptable terlipressin composition disclosed herein comprises terlipressin or a pharmaceutically acceptable salt thereof, at least one buffer salt chosen from sodium acetate and sodium benzoate, and sodium sulfate.

In some embodiments, the pharmaceutically acceptable terlipressin composition disclosed herein comprises terlipressin or a pharmaceutically acceptable salt thereof, sodium acetate, and sodium sulfate.

In some embodiments, the pharmaceutically acceptable terlipressin composition disclosed herein comprises about 0.1 mg/mL terlipressin or a pharmaceutically acceptable salt thereof, about 5 mM sodium acetate, and about 120 mM sodium sulfate, and further wherein the pharmaceutically acceptable terlipressin composition has a pH of about 5.

The present disclosure further provides pharmaceutically acceptable terlipressin compositions that consist essentially of terlipressin or a pharmaceutically acceptable salt thereof and at least one buffer salt. In some embodiments, the terlipressin compositions consists essentially of terlipressin or a pharmaceutically acceptable salt thereof and sodium acetate. In some embodiments, the terlipressin compositions consists essentially of terlipressin or a pharmaceutically acceptable salt thereof and sodium benzoate. Also, further in some embodiments, the terlipressin compositions consists essentially of about 0.1 mg/mL terlipressin or a pharmaceutically acceptable salt thereof and about 1 mM sodium acetate, and further wherein the pharmaceutically acceptable terlipressin composition has a pH of about 4.6.

Stability

As noted above, the compositions described herein exhibit good stability against the formation of impurities, including degradation products. As discussed in more detail in Example 1 below, the studies described herein identify two main degradation routes of terlipressin: (1) acid-catalyzed hydrolysis (accelerated by low pH), forming [$Gly^{12}OH$], [$Asp^8$] and [$Glu^7$]terlipressin and (2) diketopiperazine ring closure by the positively amino group of the terminal glycine residue (accelerated by high pH), forming desGly1Gly2-terlipressin. In some embodiments, the compositions are stable against the formation of impurities, including one or more or all of these degradation products, when stored at room temperature for one year or longer, including for one year, two years or three years. It is to be understood that room temperature may be 25° C. or even 30° C.

In some embodiments, the compositions described herein have improved stability as compared to the commercial GLYPRES SIN® formulation, such as may be reflected in reduced formation of impurities. For instance, in some embodiments, when stored at room temperature (e.g., at 25° C.) for 12 months, the amount in the composition of any one or more or all of the impurities listed in the below table is within the acceptance criteria set forth below.

TABLE A

| Impurity | acceptance criteria |
| --- | --- |
| Sum of degradation products | ≤3.5% |
| desGly$^1$, Gly$^2$, Gly$^3$-terlipressin | ≤0.1% |
| desGly$^1$, Gly$^2$-terlipressin | ≤1.0% |
| desGly$^1$-terlipressin | ≤1.0% |
| [Gly$^{12}$OH]terlipressin | ≤1.0% |
| [Asp$^8$]terlipressin | ≤1.0% |
| [Glu$^7$]terlipressin | ≤1.0% |
| [Ac-Gly$^1$]terlipressin | ≤1.0% |
| Any individual terlipressin dimer | ≤1.0% |
| Any individual unknown impurity | ≤0.5% |

In some embodiments, the terlipressin compositions disclosed herein, when stored at room temperature (e.g., at 25° C.) are stable for at least one year, such as about one year, about 18 months, about 24 months, about 30 months, or about 36 months. In some embodiments, stability is assessed relative to the commercial formulation GLYPRESSIN®, such as may be reflected in reduced formation of impurities as compared to levels formed in a GLYPRESSIN® formulation stored under the same conditions.

In some embodiments, the terlipressin compositions disclosed herein have a total impurity content of less than or equal to about 3.5% w/w, including less than or equal to 3.5% w/w, based on the total weight of the terlipressin, after being stored at room temperature (e.g., at 25° C.) for a period of time, such as at least one year, including a total impurity content of about 3.5% about 3.4%, about 3.3%, about 3.2%, about 3.1%, about 3.0%, about 2.9%, about 2.8%, about 2.7%, about 2.6%, about 2.5%, about 2.4%, about 2.3%, about 2.2%, about 2.1%, about 2.0%, about 1.9%, about 1.8%, about 1.7%, about 1.6%, about 1.5%, about 1.4%, about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, or about 0.1%. Non-limiting examples of total impurity content include 3.5%, 3.4%, 3.3%, 3.2%, 3.1%, 3.0%, 2.9%, 2.8%, 2.7%, 2.6%, 2.5%, 2.4%, 2.3%, 2.2%, 2.1%, 2.0%, 1.9%, 1.8%, 1.7%, 1.6%, 1.5%, 1.4%, 1.5%, 1.4%, 1.3%, 1.2%, 1.1%, 1.0%, 0.9%, 0.8%, 0.7%, 0.6%, 0.5%, 0.4%, 0.3%, 0.2%, or 0.1%.

In some embodiments, the terlipressin compositions disclosed herein have a total impurity content of less than or equal to about 1.9% w/w, including less than or equal to 1.9 w/w, based on the total weight of the terlipressin, after being stored at room temperature (e.g., at 25° C.) for a period of time, such as at least one year, including a total impurity content of about 1.9%, about 1.8%, about 1.7%, about 1.6%, about 1.5%, about 1.4%, about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, or about 0.1%. Non-limiting examples of total impurity content include 1.9%, 1.8%, 1.7%, 1.6%, 1.5%, 1.4%, 1.5%, 1.4%, 1.3%, 1.2%, 1.1%, 1.0%, 0.9%, 0.8%, 0.7%, 0.6%, 0.5%, 0.4%, 0.3%, 0.2%, or 0.1%. In some embodiments, after being stored at room temperature (e.g., at 25° C.) for a period of time, such as at least one year, the total impurity content in the composition is less than or equal to about 1.2% w/w based on the total weight of the terlipressin, including less than or equal to 1.2% w/w.

In some embodiments, the terlipressin compositions disclosed herein, have a desGly$^1$,Gly$^2$, Gly$^3$-terlipressin content of less than or equal to about 0.1% w/w, including less than or equal 0.1% w/w, based on the total weight of the terlipressin, after being stored at room temperature (e.g., at 25° C.) for a period of time, such as at least one year, including a desGly$^1$,Gly$^2$, Gly$^3$-terlipressin content of about 0.1%, about 0.09%, about 0.08%, about 0.07%, about 0.06%, about 0.05%, about 0.04%, about 0.03%, about 0.02%, or about 0.01%. Non-limiting examples of desGly$^1$, Gly$^2$, Gly$^3$-terlipressin content include 0.1%, 0.09%, 0.08%, 0.07%, 0.06%, 0.05%, 0.04%, 0.03%, 0.02%, or 0.01%.

In some embodiments, the terlipressin compositions disclosed herein, have a desGly$^1$,Gly$^2$-terlipressin content of less than or equal to about 1.0% w/w, including less than or equal 1.0% w/w, based on the total weight of the terlipressin, after being stored at room temperature (e.g., at 25° C.) for a period of time, such as at least one year, including a desGly$^1$,Gly$^2$-terlipressin content of about 1.0%, about 0.9%, about 0.8%, about 0.7%, about 0.6%, about 0.5%, about 0.4%, about 0.3%, about 0.2%, or about 0.1%. Non-limiting examples of desGly$^1$,Gly$^2$-terlipressin content include 1.0%, 0.9%, 0.8%, 0.7%, 0.6%, 0.5%, 0.4%, 0.3%, 0.2%, or 0.1%. In some embodiments, after being stored at room temperature (e.g., at 25° C.) for a period of time, such as at least one year, the desGly$^1$,Gly$^2$-terlipressin content in the composition is less than or equal to about 0.3% w/w, including less than or equal to 0.3% w/w.

In some embodiments, the terlipressin compositions disclosed herein have a desGly$^1$-terlipressin content of less than or equal to about 1.0% w/w, including less than or equal to 1.0% w/w, based on the total weight of the terlipressin, after being stored at room temperature (e.g., at 25° C.) for a period of time, such as at least one year, including a desGly$^1$-terlipressin content of about 1.0%, about 0.9%, about 0.8%, about 0.7%, about 0.6%, about 0.5%, about 0.4%, about 0.3%, about 0.2%, or about 0.1%. Non-limiting examples of desGly$^1$-terlipressin content include 1.0%, 0.9%, 0.8%, 0.7%, 0.6%, 0.5%, 0.4%, 0.3%, 0.2%, or 0.1%. In some embodiments, after being stored at room temperature (e.g., at 25° C.) for a period of time, such as at least one year, the desGly$^1$-terlipressin content in the composition is less than or equal to about 0.3% w/w, including less than or equal to 0.3% w/w.

In some embodiments, the terlipressin compositions disclosed herein, have a [Gly$^{12}$OH]terlipressin content of less than or equal to about 1.0% w/w, including less than or equal to 1.0% w/w, based on the total weight of the terlipressin, after being stored at room temperature (e.g., at 25° C.) for a period of time, such as at least one year, including a [Gly$^{12}$OH]terlipressin content of about 1.0%, about 0.9%, about 0.8%, about 0.7%, about 0.6%, about 0.5%, about 0.4%, about 0.3%, about 0.2%, or about 0.1%. Non-limiting examples of [Gly$^{12}$OH]terlipressin content include 1.0%, 0.9%, 0.8%, 0.7%, 0.6%, 0.5%, 0.4%, 0.3%, 0.2%, or 0.1%. In some embodiments, after being stored at room temperature (e.g., at 25° C.) for a period of time, such as at least one year, the [Gly$^{12}$OH]terlipressin content in the composition is less than or equal to about 0.3% w/w, including less than or equal to 0.3% w/w.

In some embodiments, the terlipressin compositions disclosed herein, have a [Asp$^8$]terlipressin content of less than or equal to about 1.0% w/w, including less than or equal to 1.0% w/w, based on the total weight of the terlipressin, after being stored at room temperature (e.g., at 25° C.) for a period of time, such as at least one year, including a [Asp$^8$]terlipressin content of about 1.0%, about 0.9%, about 0.8%, about 0.7%, about 0.6%, about 0.5%, about 0.4%, about 0.3%, about 0.2%, about 0.1%, about 0.05%. Non-limiting examples of [Asp$^8$]terlipressin content include 1.0%, 0.9%, 0.8%, 0.7%, 0.6%, 0.5%, 0.4%, 0.3%, 0.2%, 0.1%, 0.05%. In some embodiments, after being stored at room temperature (e.g., at 25° C.) for a period of time, such as at least one year, the [Asp$^8$]terlipressin content in the composition is less than or equal to about 0.05% w/w, including less than or equal to 0.05% w/w.

In some embodiments, the terlipressin compositions disclosed herein, have a [Glu$^7$]terlipressin content of less than or equal to about 1.0% w/w, including less than or equal to 1.0 w/w, based on the total weight of the terlipressin, after being stored at room temperature (e.g., at 25° C.) for a period of time, such as at least one year, including a [Glu$^7$]terlipressin content of about 1.0%, about 0.9%, about 0.8%, about 0.7%, about 0.6%, about 0.5%, about 0.4%, about 0.3%, about 0.2%, or about 0.1%. Non-limiting examples of [Glu$^7$]terlipressin content include 1.0%, 0.9%, 0.8%, 0.7%, 0.6%, 0.5%, 0.4%, 0.3%, 0.2%, or 0.1%. In some embodiments, after being stored at room temperature (e.g., at 25° C.) for a period of time, such as at least one year, the [Glu$^7$]terlipressin content in the composition is less than or equal to about 0.2% w/w, including less than or equal to 0.2% w/w.

In some embodiments, the terlipressin compositions disclosed herein, have a [Ac-Gly$^1$]terlipressin content of less than or equal to about 1.0% w/w, including less than or equal to 1.0% w/w, based on the total weight of the terlipressin, after being stored at room temperature (e.g., at 25° C.) for a period of time, such as at least one year, including a [Ac-Gly$^1$]terlipressin content of about 1.0%, about 0.9%, about 0.8%, about 0.7%, about 0.6%, about 0.5%, about 0.4%, about 0.3%, about 0.2%, or about 0.1%. Non-limiting examples of [Ac-Gly$^1$]terlipressin content include 1.0%, 0.9%, 0.8%, 0.7%, 0.6%, 0.5%, 0.4%, 0.3%, 0.2%, or 0.1%. In some embodiments, after being stored at room temperature (e.g., at 25° C.) for a period of time, such as at least one year, the [Ac-Gly$^1$]terlipressin content in the composition is less than or equal to about 0.1% w/w, including less than or equal to 0.1% w/w.

In some embodiments, the terlipressin compositions disclosed herein, have an individual terlipressin dimer content of less than or equal to about 1.0% w/w, including less than or equal to 1.0% w/w, based on the total weight of the terlipressin, after being stored at room temperature (e.g., at 25° C.) for a period of time, such as at least one year, including an individual terlipressin dimer content of about 1.0%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, or about 0.01%. Non-limiting examples of any individual terlipressin dimer content include 1.0%, 0.9%, 0.8%, 0.7%, 0.6%, 0.5%, 0.4%, 0.3%, 0.2%, 0.1%, 0.09%, 0.08%, 0.07%, 0.06%, 0.05%, 0.04%, 0.03%, 0.02%, or 0.01%. In some embodiments, after being stored at room temperature (e.g., at 25° C.) for a period of time, such as at least one year, the content of any individual terlipressin dimer in the composition is less than or equal to about 0.01% w/w, including less than or equal to 0.01% w/w.

In some embodiments, the terlipressin compositions disclosed herein, have an any other individual impurity content (e.g., any impurity other than those discussed above) of less than or equal to about 0.5% w/w, including less than or equal to 0.5 w/w, based on the total weight of the terlipressin, after being stored at room temperature (e.g., at 25° C.) for a period of time, such as at least one year, including an any other individual impurity content of about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, or about 0.01%. Non-limiting examples of any other individual impurity content include 0.5%, 0.4%, 0.3%, 0.2%, 0.1%, 0.09%, 0.08%, 0.07%, 0.06%, 0.05%, 0.04%, 0.03%, 0.02%, or 0.01%. In some embodiments, after being stored at room temperature (e.g., at 25° C.) for a period of time, such as at least one year, the content of any other individual impurity in the composition is less than about 0.05% w/w, including is less than 0.05% w/w.

In some embodiments, the terlipressin compositions disclosed herein have a total impurity content of less than or equal to about 1.9% w/w, including less than or equal to 1.9% w/w, based on the total weight of the terlipressin, after being stored at 25° C. and 60% relative humidity for a period of time, such as at least one year, including a total impurity content of about 1.9%, about 1.8%, about 1.7%, about 1.6%, about 1.5%, about 1.4%, about 1.5%, about 1.4%, about 1.3%, about 1.2%, about 1.1%, about 1.0%, about 0.9%, about 0.8%, about 0.7%, about 0.6%, about 0.5%, about 0.4%, about 0.3%, about 0.2%, or about 0.1%. Non-limiting examples of total impurity content include 1.9%, 1.8%, 1.7%, 1.6%, 1.5%, 1.4%, 1.5%, 1.4%, 1.3%, 1.2%, 1.1%, 1.0%, 0.9%, 0.8%, 0.7%, 0.6%, 0.5%, 0.4%, 0.3%, 0.2%, or 0.1%. In some embodiments, after being stored at 25° C. and 60% relative humidity for a period of time, such as at least one year, the total impurity content in the composition is less than or equal to about 1.2% w/w based on the total weight of the terlipressin, including less than or equal to 1.2% w/w. In some embodiments, the period of time is selected from one year, 18 months, 24 months, and 36 months. In some embodiments, the period of time is 12 months. In some embodiments, the period of time is 24 months. In some embodiments, the period of time is 36 months.

In some embodiments, the terlipressin compositions disclosed herein, when stored at room temperature (e.g., at 25° C. or 30° C.) for a period of time, such as about 1 months, about 3 months, about 6 months, about 9 months, about 12 months, about 18 months, or about 2 years, the total impurity formed in the terlipressin compositions is less than about 3.5% by weight relative to the total weight of the terlipressin. In some embodiments, the terlipressin compositions disclosed herein, when stored at room temperature (e.g., at 25° C. or 30° C.) for a period of time, such as about 1 months, about 3 months, about 6 months, about 9 months, about 12 months, about 18 months, or about 2 years, the total impurity formed in the terlipressin compositions is less than about 1.9% by weight relative to the total weight of the terlipressin.

In some embodiments, the composition comprises terlipressin acetate in an amount to provide 0.1 mg/mL terlipressin free base, sodium acetate in an amount to provide a total acetate concentration of about 1 mM, sodium chloride at a concentration of about 9 mg/mL, and water, and has a total impurity content of less than or equal to about 1.9% w/w after being stored at room temperature (e.g., at 25° C.) for a period of time of at least one year. Additionally or alternatively, such a composition may have a desGly¹,Gly², Gly³-terlipressin content of less than or equal to about 0.1% w/w, after being stored at room temperature (e.g., at 25° C.) for a period of time of at least one year. Additionally or alternatively, such a composition may have a desGly¹,Gly²-terlipressin content of less than or equal to about 1.0% w/w, after being stored at room temperature (e.g., at 25° C.) for a period of time of at least one year. Additionally, or alternatively, such a composition may have a desGly¹-terlipressin content of less than or equal to about 1.0% w/w, after being stored at room temperature (e.g., at 25° C.) for a period of time of at least one year. Additionally or alternatively, such a composition may have a [Gly¹²OH]terlipressin content of less than or equal to about 1.0% w/w, after being stored at room temperature (e.g., at 25° C.) for a period of time of at least one year. Additionally or alternatively, such a composition may have a [Asp⁸]terlipressin content of less than or equal to about 1.0% w/w, after being stored at room temperature (e.g., at 25° C.) for a period of time of at least one year. Additionally or alternatively, such a composition may have a [Glu⁷]terlipressin content of less than or equal to about 1.0% w/w, after being stored at room temperature (e.g., at 25° C.) for a period of time of at least one year. Additionally or alternatively, such a composition may have a [Ac-Gly¹]terlipressin content of less than or equal to about 1.0% w/w, after being stored at room temperature (e.g., at 25° C.) for a period of time of at least one year. Additionally, or alternatively, such a composition may have an individual terlipressin dimer content of less than or equal to about 1.0% w/w, after being stored at room temperature (e.g., at 25° C.) for a period of time of at least one year. Additionally, or alternatively, such a composition may have any other individual impurity content (e.g., any impurity other than those discussed above) of less than or equal to about 0.5% w/w, after being stored at room temperature (e.g., at 25° C.) for a period of time of at least one year. In any of these embodiments, the composition may have a pH of 4.8±0.3.

In some embodiments, the composition comprises terlipressin acetate in an amount to provide 1.0 mg/mL terlipressin free base, sodium acetate in an amount to provide a total acetate concentration of about 1 mM, sodium chloride at a concentration of about 9 mg/mL, and water, and has a total impurity content of less than or equal to about 1.9% w/w after being stored at room temperature (e.g., at 25° C.) for a period of time of at least one year. Additionally or alternatively, such a composition may have a desGly¹,Gly², Gly³-terlipressin content of less than or equal to about 0.1% w/w, after being stored at room temperature (e.g., at 25° C.) for a period of time of at least one year. Additionally or alternatively, such a composition may have a desGly¹,Gly²-terlipressin content of less than or equal to about 1.0% w/w, after being stored at room temperature (e.g., at 25° C.) for a period of time of at least one year. Additionally, or alternatively, such a composition may have a desGly¹-terlipressin content of less than or equal to about 1.0% w/w, after being stored at room temperature (e.g., at 25° C.) for a period of time of at least one year. Additionally or alternatively, such a composition may have a [Gly¹²OH]terlipressin content of less than or equal to about 1.0% w/w, after being stored at room temperature (e.g., at 25° C.) for a period of time of at least one year. Additionally or alternatively, such a composition may have a [Asp⁸]terlipressin content of less than or equal to about 1.0% w/w, after being stored at room temperature (e.g., at 25° C.) for a period of time of at least one year. Additionally or alternatively, such a composition may have a [Glu⁷]terlipressin content of less than or equal to about 1.0% w/w, after being stored at room temperature (e.g., at 25° C.) for a period of time of at least one year. Additionally or alternatively, such a composition may have a [Ac-Gly¹]terlipressin content of less than or equal to about 1.0% w/w, after being stored at room temperature (e.g., at 25° C.) for a period of time of at least one year. Additionally, or alternatively, such a composition may have an individual terlipressin dimer content of less than or equal to about 1.0% w/w, after being stored at room temperature (e.g., at 25° C.) for a period of time of at least one year. Additionally, or alternatively, such a composition may have any other individual impurity content (e.g., any impurity other than those discussed above) of less than or equal to about 0.5% w/w, after being stored at room temperature (e.g., at 25° C.) for a period of time of at least one year. In any of these embodiments, the composition may have a pH of 4.8±0.3.

In some embodiments, the composition comprises terlipressin acetate in an amount to provide 2.0 mg/mL terlipressin free base, sodium acetate in an amount to provide a total acetate concentration of about 1 mM, sodium chloride at a concentration of about 9 mg/mL, and water, and has a total impurity content of less than or equal to about 1.9% w/w after being stored at room temperature (e.g., at 25° C.) for a period of time of at least one year. Additionally or alternatively, such a composition may have a desGly¹,Gly², Gly³-terlipressin content of less than or equal to about 0.1% w/w, after being stored at room temperature (e.g., at 25° C.) for a period of time of at least one year. Additionally or alternatively, such a composition may have a desGly¹,Gly²-terlipressin content of less than or equal to about 1.0% w/w, after being stored at room temperature (e.g., at 25° C.) for a period of time of at least one year. Additionally, or alternatively, such a composition may have a desGly¹-terlipressin content of less than or equal to about 1.0% w/w, after being stored at room temperature (e.g., at 25° C.) for a period of time of at least one year. Additionally or alternatively, such a composition may have a [Gly¹²OH]terlipressin content of less than or equal to about 1.0% w/w, after being stored at room temperature (e.g., at 25° C.) for a period of time of at least one year. Additionally or alternatively, such a composition may have a [Asp⁸]terlipressin content of less than or equal to about 1.0% w/w, after being stored at room temperature (e.g., at 25° C.) for a period of time of at least one year. Additionally or alternatively, such a composition may have a [Glu⁷]terlipressin content of less than or equal to about 1.0% w/w, after being stored at room temperature (e.g., at 25° C.) for a period of time of at least one year. Additionally or alternatively, such a composition may have a [Ac-Gly¹]terlipressin content of less than or equal to about 1.0% w/w, after being stored at room temperature (e.g., at 25° C.) for a period of time of at least one year. Additionally, or alternatively, such a composition may have an individual terlipressin dimer content of less than or equal to about 1.0% w/w, after being stored at room temperature (e.g., at 25° C.) for a period of time of at least one year. Additionally, or alternatively, such a composition may have any other individual impurity content (e.g., any impurity other than those discussed above) of less than or equal to about 0.5% w/w, after being stored at room temperature (e.g., at 25° C.) for a period of time of at least one year. In any of these embodiments, the composition may have a pH of 4.8±0.3.

In some embodiments, the composition comprises terlipressin acetate in an amount to provide 3.0 mg/mL terlipressin free base, sodium acetate in an amount to provide a total acetate concentration of about 1 mM, sodium chloride at a concentration of about 9 mg/mL, and water, and has a total impurity content of less than or equal to about 1.9% w/w after being stored at room temperature (e.g., at 25° C.) for a period of time of at least one year. Additionally or alternatively, such a composition may have a desGly$^1$,Gly$^2$, Gly$^3$-terlipressin content of less than or equal to about 0.1% w/w, after being stored at room temperature (e.g., at 25° C.) for a period of time of at least one year. Additionally or alternatively, such a composition may have a desGly$^1$,Gly$^2$-terlipressin content of less than or equal to about 1.0% w/w, after being stored at room temperature (e.g., at 25° C.) for a period of time of at least one year. Additionally, or alternatively, such a composition may have a desGly$^1$-terlipressin content of less than or equal to about 1.0% w/w, after being stored at room temperature (e.g., at 25° C.) for a period of time of at least one year. Additionally or alternatively, such a composition may have a [Gly$^{12}$OH]terlipressin content of less than or equal to about 1.0% w/w, after being stored at room temperature (e.g., at 25° C.) for a period of time of at least one year. Additionally or alternatively, such a composition may have a [Asp$^8$]terlipressin content of less than or equal to about 1.0% w/w, after being stored at room temperature (e.g., at 25° C.) for a period of time of at least one year. Additionally or alternatively, such a composition may have a [Glu$^7$]terlipressin content of less than or equal to about 1.0% w/w, after being stored at room temperature (e.g., at 25° C.) for a period of time of at least one year. Additionally or alternatively, such a composition may have a [Ac-Gly$^1$]terlipressin content of less than or equal to about 1.0% w/w, after being stored at room temperature (e.g., at 25° C.) for a period of time of at least one year. Additionally, or alternatively, such a composition may have an individual terlipressin dimer content of less than or equal to about 1.0% w/w, after being stored at room temperature (e.g., at 25° C.) for a period of time of at least one year. Additionally, or alternatively, such a composition may have any other individual impurity content (e.g., any impurity other than those discussed above) of less than or equal to about 0.5% w/w, after being stored at room temperature (e.g., at 25° C.) for a period of time of at least one year. In any of these embodiments, the composition may have a pH of 4.8±0.3.

In some embodiments, the composition comprises terlipressin acetate in an amount to provide 4.0 mg/mL terlipressin free base, sodium acetate in an amount to provide a total acetate concentration of about 1 mM, sodium chloride at a concentration of about 9 mg/mL, and water, and has a total impurity content of less than or equal to about 1.9% w/w after being stored at room temperature (e.g., at 25° C.) for a period of time of at least one year. Additionally or alternatively, such a composition may have a desGly$^1$,Gly$^2$, Gly$^3$-terlipressin content of less than or equal to about 0.1% w/w, after being stored at room temperature (e.g., at 25° C.) for a period of time of at least one year. Additionally or alternatively, such a composition may have a desGly$^1$,Gly$^2$-terlipressin content of less than or equal to about 1.0% w/w, after being stored at room temperature (e.g., at 25° C.) for a period of time of at least one year. Additionally, or alternatively, such a composition may have a desGly$^1$-terlipressin content of less than or equal to about 1.0% w/w, after being stored at room temperature (e.g., at 25° C.) for a period of time of at least one year. Additionally or alternatively, such a composition may have a [Gly$^{12}$OH]terlipressin content of less than or equal to about 1.0% w/w, after being stored at room temperature (e.g., at 25° C.) for a period of time of at least one year. Additionally or alternatively, such a composition may have a [Asp$^8$]terlipressin content of less than or equal to about 1.0% w/w, after being stored at room temperature (e.g., at 25° C.) for a period of time of at least one year. Additionally or alternatively, such a composition may have a [Glu$^7$]terlipressin content of less than or equal to about 1.0% w/w, after being stored at room temperature (e.g., at 25° C.) for a period of time of at least one year. Additionally or alternatively, such a composition may have a [Ac-Gly$^1$]terlipressin content of less than or equal to about 1.0% w/w, after being stored at room temperature (e.g., at 25° C.) for a period of time of at least one year. Additionally, or alternatively, such a composition may have an individual terlipressin dimer content of less than or equal to about 1.0% w/w, after being stored at room temperature (e.g., at 25° C.) for a period of time of at least one year. Additionally, or alternatively, such a composition may have any other individual impurity content (e.g., any impurity other than those discussed above) of less than or equal to about 0.5% w/w, after being stored at room temperature (e.g., at 25° C.) for a period of time of at least one year. In any of these embodiments, the composition may have a pH of 4.8±0.3.

In some embodiments, the composition comprises terlipressin acetate in an amount to provide 5.0 mg/mL terlipressin free base, sodium acetate in an amount to provide a total acetate concentration of about 1 mM, sodium chloride at a concentration of about 9 mg/mL, and water, and has a total impurity content of less than or equal to about 1.9% w/w after being stored at room temperature (e.g., at 25° C.) for a period of time of at least one year. Additionally or alternatively, such a composition may have a desGly$^1$,Gly$^2$, Gly$^3$-terlipressin content of less than or equal to about 0.1% w/w, after being stored at room temperature (e.g., at 25° C.) for a period of time of at least one year. Additionally or alternatively, such a composition may have a desGly$^1$,Gly$^2$-terlipressin content of less than or equal to about 1.0% w/w, after being stored at room temperature (e.g., at 25° C.) for a period of time of at least one year. Additionally, or alternatively, such a composition may have a desGly$^1$-terlipressin content of less than or equal to about 1.0% w/w, after being stored at room temperature (e.g., at 25° C.) for a period of time of at least one year. Additionally or alternatively, such a composition may have a [Gly$^{12}$OH]terlipressin content of less than or equal to about 1.0% w/w, after being stored at room temperature (e.g., at 25° C.) for a period of time of at least one year. Additionally or alternatively, such a composition may have a [Asp$^8$]terlipressin content of less than or equal to about 1.0% w/w, after being stored at room temperature (e.g., at 25° C.) for a period of time of at least one year. Additionally or alternatively, such a composition may have a [Glu$^7$]terlipressin content of less than or equal to about 1.0% w/w, after being stored at room temperature (e.g., at 25° C.) for a period of time of at least one year. Additionally or alternatively, such a composition may have a [Ac-Gly$^1$]terlipressin content of less than or equal to about 1.0% w/w, after being stored at room temperature (e.g., at 25° C.) for a period of time of at least one year. Additionally, or alternatively, such a composition may have an individual terlipressin dimer content of less than or equal to about 1.0% w/w, after being stored at room temperature (e.g., at 25° C.) for a period of time of at least one year. Additionally, or alternatively, such a composition may have any other individual impurity content (e.g., any impurity other than those discussed above) of less than or equal to about 0.5% w/w, after being stored at room temperature (e.g., at 25° C.) for a period of time of at least one year. In any of these embodiments, the composition may have a pH of 4.8±0.3.

In some embodiments, the composition comprises terlipressin acetate in an amount to provide 0.1 mg/mL terlipressin free base, sodium acetate in an amount to provide a total acetate concentration of about 1 mM, and water, and has a total impurity content of less than or equal to about 1.9% w/w after being stored at room temperature (e.g., at 25° C.) for a period of time of at least one year. Additionally or alternatively, such a composition may have a desGly$^1$,Gly$^2$, Gly$^3$-terlipressin content of less than or equal to about 0.1% w/w, after being stored at room temperature (e.g., at 25° C.) for a period of time of at least one year. Additionally or alternatively, such a composition may have a desGly$^1$,Gly$^2$-terlipressin content of less than or equal to about 1.0% w/w, after being stored at room temperature (e.g., at 25° C.) for a period of time of at least one year. Additionally, or alternatively, such a composition may have a desGly$^1$-terlipressin content of less than or equal to about 1.0% w/w, after being stored at room temperature (e.g., at 25° C.) for a period of time of at least one year. Additionally or alternatively, such a composition may have a [Gly$^{12}$OH]terlipressin content of less than or equal to about 1.0% w/w, after being stored at room temperature (e.g., at 25° C.) for a period of time of at least one year. Additionally or alternatively, such a composition may have a [Asp$^8$]terlipressin content of less than or equal to about 1.0% w/w, after being stored at room temperature (e.g., at 25° C.) for a period of time of at least one year. Additionally or alternatively, such a composition may have a [Glu$^7$]terlipressin content of less than or equal to about 1.0% w/w, after being stored at room temperature (e.g., at 25° C.) for a period of time of at least one year. Additionally or alternatively, such a composition may have a [Ac-Gly$^1$]terlipressin content of less than or equal to about 1.0% w/w, after being stored at room temperature (e.g., at 25° C.) for a period of time of at least one year. Additionally, or alternatively, such a composition may have an individual terlipressin dimer content of less than or equal to about 1.0% w/w, after being stored at room temperature (e.g., at 25° C.) for a period of time of at least one year. Additionally, or alternatively, such a composition may have any other individual impurity content (e.g., any impurity other than those discussed above) of less than or equal to about 0.5% w/w, after being stored at room temperature (e.g., at 25° C.) for a period of time of at least one year. In any of these embodiments, the composition may have a pH of 4.8±0.3.

In some embodiments, the composition comprises terlipressin acetate in an amount to provide 1.0 mg/mL terlipressin free base, sodium acetate in an amount to provide a total acetate concentration of about 1 mM, and water, and has a total impurity content of less than or equal to about 1.9% w/w after being stored at room temperature (e.g., at 25° C.) for a period of time of at least one year. Additionally or alternatively, such a composition may have a desGly$^1$,Gly$^2$, Gly$^3$-terlipressin content of less than or equal to about 0.1% w/w, after being stored at room temperature (e.g., at 25° C.) for a period of time of at least one year. Additionally or alternatively, such a composition may have a desGly$^1$,Gly$^2$-terlipressin content of less than or equal to about 1.0% w/w, after being stored at room temperature (e.g., at 25° C.) for a period of time of at least one year. Additionally, or alternatively, such a composition may have a desGly$^1$-terlipressin content of less than or equal to about 1.0% w/w, after being stored at room temperature (e.g., at 25° C.) for a period of time of at least one year. Additionally or alternatively, such a composition may have a [Gly$^{12}$OH]terlipressin content of less than or equal to about 1.0% w/w, after being stored at room temperature (e.g., at 25° C.) for a period of time of at least one year. Additionally or alternatively, such a composition may have a [Asp$^8$]terlipressin content of less than or equal to about 1.0% w/w, after being stored at room temperature (e.g., at 25° C.) for a period of time of at least one year. Additionally or alternatively, such a composition may have a [Glu$^7$]terlipressin content of less than or equal to about 1.0% w/w, after being stored at room temperature (e.g., at 25° C.) for a period of time of at least one year. Additionally or alternatively, such a composition may have a [Ac-Gly$^1$]terlipressin content of less than or equal to about 1.0% w/w, after being stored at room temperature (e.g., at 25° C.) for a period of time of at least one year. Additionally, or alternatively, such a composition may have an individual terlipressin dimer content of less than or equal to about 1.0% w/w, after being stored at room temperature (e.g., at 25° C.) for a period of time of at least one year. Additionally, or alternatively, such a composition may have any other individual impurity content (e.g., any impurity other than those discussed above) of less than or equal to about 0.5% w/w, after being stored at room temperature (e.g., at 25° C.) for a period of time of at least one year. In any of these embodiments, the composition may have a pH of 4.8±0.3.

In some embodiments, the composition comprises terlipressin acetate in an amount to provide 2.0 mg/mL terlipressin free base, sodium acetate in an amount to provide a total acetate concentration of about 1 mM, and water, and has a total impurity content of less than or equal to about 1.9% w/w after being stored at room temperature (e.g., at 25° C.) for a period of time of at least one year. Additionally or alternatively, such a composition may have a desGly$^1$,Gly$^2$, Gly$^3$-terlipressin content of less than or equal to about 0.1% w/w, after being stored at room temperature (e.g., at 25° C.) for a period of time of at least one year. Additionally or alternatively, such a composition may have a desGly$^1$,Gly$^2$-terlipressin content of less than or equal to about 1.0% w/w, after being stored at room temperature (e.g., at 25° C.) for a period of time of at least one year. Additionally, or alternatively, such a composition may have a desGly$^1$-terlipressin content of less than or equal to about 1.0% w/w, after being stored at room temperature (e.g., at 25° C.) for a period of time of at least one year. Additionally or alternatively, such a composition may have a [Gly$^{12}$OH]terlipressin content of less than or equal to about 1.0% w/w, after being stored at room temperature (e.g., at 25° C.) for a period of time of at least one year. Additionally or alternatively, such a composition may have a [Asp$^8$]terlipressin content of less than or equal to about 1.0% w/w, after being stored at room temperature (e.g., at 25° C.) for a period of time of at least one year. Additionally or alternatively, such a composition may have a [Glu$^7$]terlipressin content of less than or equal to about 1.0% w/w, after being stored at room temperature (e.g., at 25° C.) for a period of time of at least one year. Additionally or alternatively, such a composition may have a [Ac-Gly$^1$]terlipressin content of less than or equal to about 1.0% w/w, after being stored at room temperature (e.g., at 25° C.) for a period of time of at least one year. Additionally, or alternatively, such a composition may have an individual terlipressin dimer content of less than or equal to about 1.0% w/w, after being stored at room temperature (e.g., at 25° C.) for a period of time of at least one year. Additionally, or alternatively, such a composition may have any other individual impurity content (e.g., any impurity other than those discussed above) of less than or equal to about 0.5% w/w, after being stored at room temperature (e.g., at 25° C.) for a period of time of at least one year. In any of these embodiments, the composition may have a pH of 4.8±0.3.

In some embodiments, the composition comprises terlipressin acetate in an amount to provide 3.0 mg/mL terlipressin free base, sodium acetate in an amount to provide a total acetate concentration of about 1 mM, and water, and has a total impurity content of less than or equal to about 1.9% w/w after being stored at room temperature (e.g., at 25° C.) for a period of time of at least one year. Additionally or alternatively, such a composition may have a desGly$^1$,Gly$^2$, Gly$^3$-terlipressin content of less than or equal to about 0.1% w/w, after being stored at room temperature (e.g., at 25° C.) for a period of time of at least one year. Additionally or alternatively, such a composition may have a desGly$^1$,Gly$^2$-terlipressin content of less than or equal to about 1.0% w/w, after being stored at room temperature (e.g., at 25° C.) for a period of time of at least one year. Additionally, or alternatively, such a composition may have a desGly$^1$-terlipressin content of less than or equal to about 1.0% w/w, after being stored at room temperature (e.g., at 25° C.) for a period of time of at least one year. Additionally or alternatively, such a composition may have a [Gly$^{12}$OH]terlipressin content of less than or equal to about 1.0% w/w, after being stored at room temperature (e.g., at 25° C.) for a period of time of at least one year. Additionally or alternatively, such a composition may have a [Asp$^8$]terlipressin content of less than or equal to about 1.0% w/w, after being stored at room temperature (e.g., at 25° C.) for a period of time of at least one year. Additionally or alternatively, such a composition may have a [Glu$^7$]terlipressin content of less than or equal to about 1.0% w/w, after being stored at room temperature (e.g., at 25° C.) for a period of time of at least one year. Additionally or alternatively, such a composition may have a [Ac-Gly$^1$]terlipressin content of less than or equal to about 1.0% w/w, after being stored at room temperature (e.g., at 25° C.) for a period of time of at least one year. Additionally, or alternatively, such a composition may have an individual terlipressin dimer content of less than or equal to about 1.0% w/w, after being stored at room temperature (e.g., at 25° C.) for a period of time of at least one year. Additionally, or alternatively, such a composition may have any other individual impurity content (e.g., any impurity other than those discussed above) of less than or equal to about 0.5% w/w, after being stored at room temperature (e.g., at 25° C.) for a period of time of at least one year. In any of these embodiments, the composition may have a pH of 4.8±0.3.

In some embodiments, the composition comprises terlipressin acetate in an amount to provide 4.0 mg/mL terlipressin free base, sodium acetate in an amount to provide a total acetate concentration of about 1 mM, and water, and has a total impurity content of less than or equal to about 1.9% w/w after being stored at room temperature (e.g., at 25° C.) for a period of time of at least one year. Additionally or alternatively, such a composition may have a desGly$^1$,Gly$^2$, Gly$^3$-terlipressin content of less than or equal to about 0.1% w/w, after being stored at room temperature (e.g., at 25° C.) for a period of time of at least one year. Additionally or alternatively, such a composition may have a desGly$^1$,Gly$^2$-terlipressin content of less than or equal to about 1.0% w/w, after being stored at room temperature (e.g., at 25° C.) for a period of time of at least one year. Additionally, or alternatively, such a composition may have a desGly$^1$-terlipressin content of less than or equal to about 1.0% w/w, after being stored at room temperature (e.g., at 25° C.) for a period of time of at least one year. Additionally or alternatively, such a composition may have a [Gly$^{12}$OH]terlipressin content of less than or equal to about 1.0% w/w, after being stored at room temperature (e.g., at 25° C.) for a period of time of at least one year. Additionally or alternatively, such a composition may have a [Asp$^8$]terlipressin content of less than or equal to about 1.0% w/w, after being stored at room temperature (e.g., at 25° C.) for a period of time of at least one year. Additionally or alternatively, such a composition may have a [Glu$^7$]terlipressin content of less than or equal to about 1.0% w/w, after being stored at room temperature (e.g., at 25° C.) for a period of time of at least one year. Additionally or alternatively, such a composition may have a [Ac-Gly$^1$]terlipressin content of less than or equal to about 1.0% w/w, after being stored at room temperature (e.g., at 25° C.) for a period of time of at least one year. Additionally, or alternatively, such a composition may have an individual terlipressin dimer content of less than or equal to about 1.0% w/w, after being stored at room temperature (e.g., at 25° C.) for a period of time of at least one year. Additionally, or alternatively, such a composition may have any other individual impurity content (e.g., any impurity other than those discussed above) of less than or equal to about 0.5% w/w, after being stored at room temperature (e.g., at 25° C.) for a period of time of at least one year. In any of these embodiments, the composition may have a pH of 4.8±0.3.

In some embodiments, the composition comprises terlipressin acetate in an amount to provide 5.0 mg/mL terlipressin free base, sodium acetate in an amount to provide a total acetate concentration of about 1 mM, and water, and has a total impurity content of less than or equal to about 1.9% w/w after being stored at room temperature (e.g., at 25° C.) for a period of time of at least one year. Additionally or alternatively, such a composition may have a desGly$^1$,Gly$^2$, Gly$^3$-terlipressin content of less than or equal to about 0.1% w/w, after being stored at room temperature (e.g., at 25° C.) for a period of time of at least one year. Additionally or alternatively, such a composition may have a desGly$^1$,Gly$^2$-terlipressin content of less than or equal to about 1.0% w/w, after being stored at room temperature (e.g., at 25° C.) for a period of time of at least one year. Additionally, or alternatively, such a composition may have a desGly$^1$-terlipressin content of less than or equal to about 1.0% w/w, after being stored at room temperature (e.g., at 25° C.) for a period of time of at least one year. Additionally or alternatively, such a composition may have a [Gly$^{12}$OH]terlipressin content of less than or equal to about 1.0% w/w, after being stored at room temperature (e.g., at 25° C.) for a period of time of at least one year. Additionally or alternatively, such a composition may have a [Asp$^8$]terlipressin content of less than or equal to about 1.0% w/w, after being stored at room temperature (e.g., at 25° C.) for a period of time of at least one year. Additionally or alternatively, such a composition may have a [Glu$^7$]terlipressin content of less than or equal to about 1.0% w/w, after being stored at room temperature (e.g., at 25° C.) for a period of time of at least one year. Additionally or alternatively, such a composition may have a [Ac-Gly$^1$]terlipressin content of less than or equal to about 1.0% w/w, after being stored at room temperature (e.g., at 25° C.) for a period of time of at least one year. Additionally, or alternatively, such a composition may have an individual terlipressin dimer content of less than or equal to about 1.0% w/w, after being stored at room temperature (e.g., at 25° C.) for a period of time of at least one year. Additionally, or alternatively, such a composition may have any other individual impurity content (e.g., any impurity other than those discussed above) of less than or equal to about 0.5% w/w, after being stored at room temperature (e.g., at 25° C.) for a period of time of at least one year. In any of these embodiments, the composition may have a pH of 4.8±0.3.

Methods/Uses

The present disclosure also provides methods of treatment comprising administering a pharmaceutically acceptable terlipressin composition as described herein to a subject in need thereof, such as for treating a subject suffering from cirrhosis and/or treating hepatorenal syndrome (HRS), acute kidney injury, and/or esophageal bleeding (EVB). In some embodiments, the method is for treating hepatorenal syndrome (HRS). In some embodiments, the method is for treating acute kidney injury. In some embodiments, the method is for treating esophageal bleeding (EVB) or bleeding oesophageal varices. In some embodiments, the administering is by intravenous injection.

The present disclosure also provides any composition disclosed herein for use in treating a condition selected from hepatorenal syndrome (HRS), esophageal bleeding (EVB), and/or acute kidney injury. Such compositions may comprise 1 mg/mL, 2 mg/mL, 3 mg/mL, or 4 mg/mL terlipressin or a pharmaceutically acceptable salt thereof.

The present disclosure also provides uses of terlipressin or a pharmaceutically acceptable salt thereof in the preparation of a medicament for treating hepatorenal syndrome (HRS), esophageal bleeding (EVB), and/or acute kidney injury, wherein the medicament comprises any of the terlipressin compositions described herein. Such uses include the use of a higher dose of terlipressin or a pharmaceutically acceptable salt thereof, wherein the higher dose may be 1 mg/mL, 2 mg/mL, 3 mg/mL, or 4 mg/mL terlipressin or a pharmaceutically acceptable salt thereof.

EXAMPLES

The following specific examples are included as illustrative of the compositions described herein. These examples are in no way intended to limit the scope of the disclosure. Other aspects of the disclosure will be apparent to those skilled in the art to which the disclosure pertains.

Example 1

Formulations containing 0.1 mg/mL of terlipressin with different pH, buffer amounts, and buffer salt, as shown below were prepared according to a factorial design and stored at 25° C./60% RH for 6 months. The amounts of terlipressin and impurities were determined using ultra-performance liquid chromatographic (UPLC) method.

TABLE 1

|  | Low level | Center point | High level |
| --- | --- | --- | --- |
| pH | 4.5 | 5.0 | 5.5 |
| Amount of acetate buffer (mM) | 5 | 20 | 35 |
| Buffer salt | Acetate | Citrate | Succinate |

At the end of study, it was found that citrate and succinate reacted with terlipressin and led to high impurity levels. Based on this study, it was confirmed that acetate was a suitable buffer salt for terlipressin.

From this study, it was known that there are two main degradation routes of terlipressin:
1. acid-catalyzed hydrolysis (accelerated by low pH), forming [$Gly^{12}OH$], [$Asp^8$] and [$Glu^7$]terlipressin.
2. diketopiperazine ring closure by the positively amino group of the terminal glycine residue (accelerated by high pH), forming desGly1Gly2-terlipressin.

The acid-catalyzed hydrolysis pathway (1) may be controlled by adjusting pH to about pH 5. The diketopiperazine pathway (2) may be more difficult to control since the reaction route is "built in" the molecule. In addition, increasing pH to control degradation pathway (1) may accelerate the degradation pathway (2). Lowering the buffer concentration may result in lower amount of desGly$^1$Gly$^2$-terlipressin. However, at the buffer level of 5 mM, the diketopiperazine reaction may be too fast to control. In this pH-range, the stability limiting degradation pathway was found to be the diketopiperazine ring formation of the N-terminal glycine residue, forming the impurity desGly1Gly2-terlipressin. Preliminary studies reported in Examples 2-4 below indicate that the diketopiperazine pathway could be slowed down by using a low buffer strength and to some extent by the addition of sodium sulfate as stabilizer.

Example 2

Three 0.1 mg/mL terlipressin formulations were prepared:
1. 5 mM acetate buffer pH 5.0;
2. 5 mM acetate buffer pH 5.0+0.12M sodium sulfate; and
3. No buffer and 0.12 M ammonium sulfate, adjusted to pH 5.0

The formulations were placed at 50° C. and analyzed for the content of desGly$^1$Gly$^2$-terlipressin after 0, 1, 2, 4 and 8 days of storage. The results are as follows:
Amount of desGly$^1$Gly$^2$-terlipressin

TABLE 2

| Formulation | Initial | 1 day | 2 days | 4 days | 8 days |
| --- | --- | --- | --- | --- | --- |
| Formulation 1 | <0.05% | 0.08% | 0.12% | 0.17% | 0.33% |
| Formulation 2 | <0.05% | 0.07% | 0.09% | 0.13% | 0.25% |
| Formulation 3 | <0.05% | 0.06% | 0.08% | 0.11% | 0.22% |

This study showed that the addition of sulfate ion decreased the diketopiperazine reaction (i.e., compare Formulation 2 and 3 to Formulation 1). While formulation 3 did not contain any buffer, which would likely be an issue for pH-stability, the amount of desGly$^1$Gly$^2$-terlipressin formed at the end of 8 days storage was lower than that in Formulation 1.

Example 3

The following two formulations were stored at 25° C./65%RH for 26 weeks.
0.1 mg/mL of terlipressin, 20 mM of acetate buffer, pH 3.7 and sodium chloride (Comparative Formulation); and
0.1 mg/mL of terlipressin, 0.12M sodium sulfate, and pH 5.0 (Formulation A)

The results in FIG. 1 shows that Formulation A containing sodium sulfate had lower impurities than the Comparative Formulation. Extrapolation of data indicates that Formulation A will likely have impurities lower than 3.5% when stored at 25° C./65% RH for 156 weeks (3 years). The slope of the two curves indicate that the degradation rate is about seven times higher in the Comparative Formulation compared to Formulation A (0.1077/0.0158).

Example 4

Terlipressin formulations were prepared according to a factorial design, see table below:

TABLE 3

|  | Low level | Center point | High level |
| --- | --- | --- | --- |
| pH | 4.6 | 5.0 | 5.4 |
| Amount of acetate buffer (mM) | 1 | 5 | 9 |
| Amount of sulfate (mM) | 0 | 40 | 80 |

Comparative Formulation as described in Example 3 was also included in this study for comparison.

Figure 2:
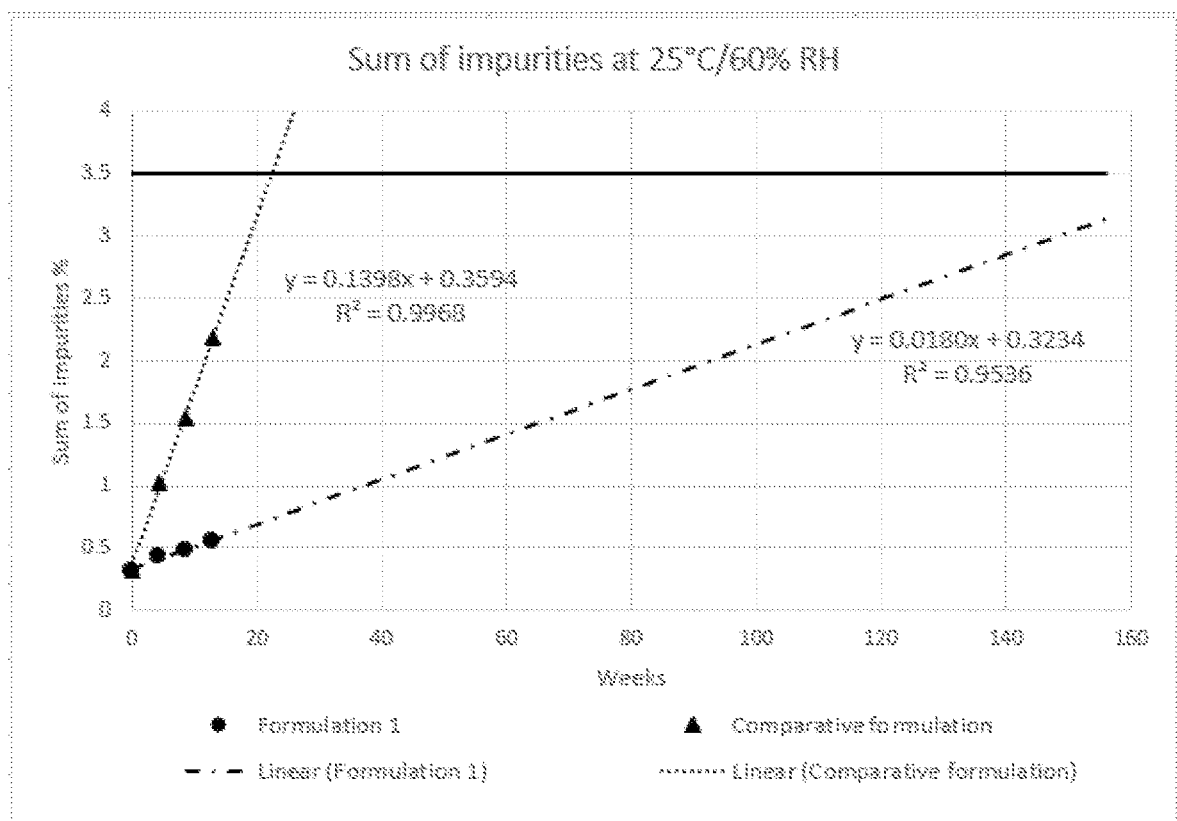
FIG. 2 is a graphical depiction of the sum of impurities for Formulation 1 and a Comparative Formula under storage at 25° C./60% RH.
Figure 3:
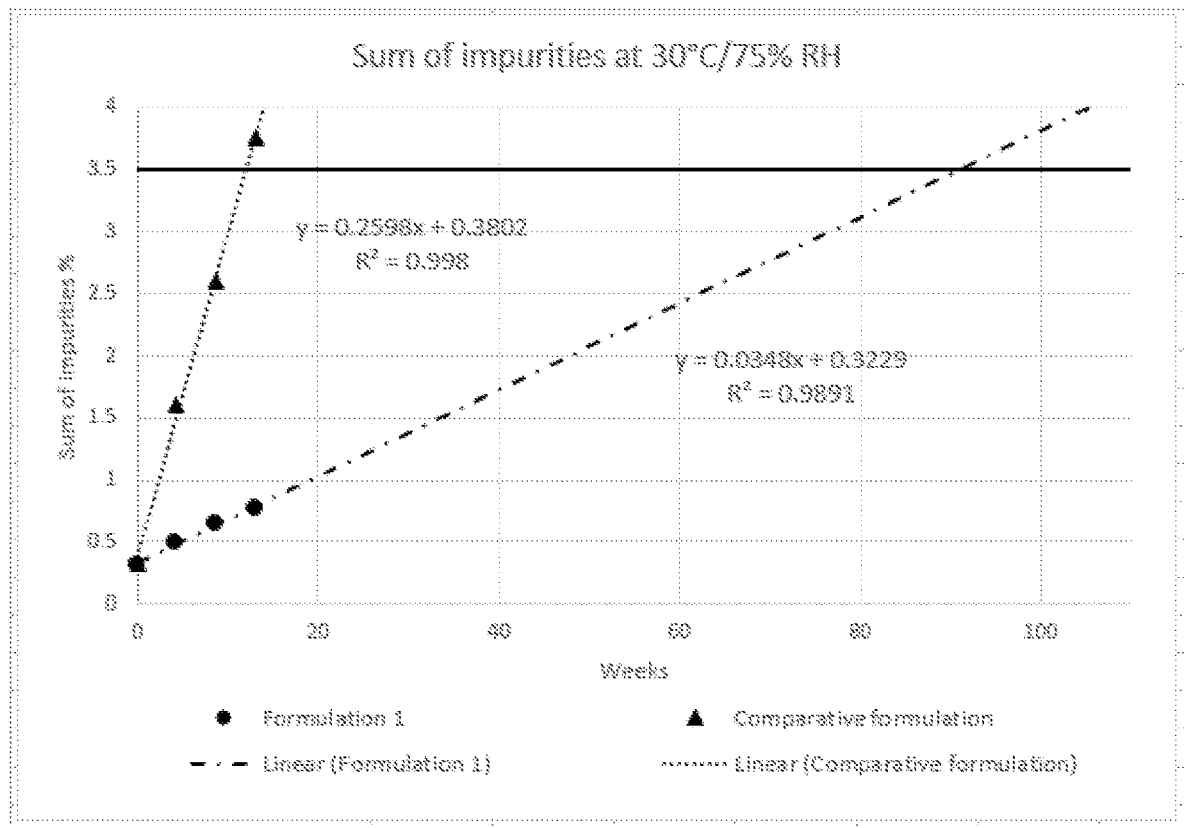
FIG. 3 is a graphical depiction of the sum of impurities for Formulation 1 and a Comparative Formula under storage at 30° C./75% RH.

These formulations were stored at 25° C./60% RH and 30° C./75% RH for three months and the results showed that the most stable formulation was the formulation with the lowest pH, the lowest amount of acetate buffer, and no sodium sulfate, referred herein as Formulation 1. The FIG. 2 and FIG. 3 show the Sum of Impurities of Formulation 1 compared to the Comparative Formulation at both 25° C./60% RH (FIG. 2) and 30° C./75% RH (FIG. 3).

The slope of the two curves indicate that the degradation rate is about seven times higher in the Comparative Formulation compared to Formulation 1 at both 25° C./60% RH and 30° C./75% RH, (0.1398/0.0180) and (0.2598/0.0348), respectively.

This study shows that lowering the acetate content may improve the overall stability of terlipressin composition. The stabilizing effect of sulfate is more apparent at the acetate concentrations of 5 and 9 mM but is almost non-existing at the low acetate concentration of 1 mM.

Example 5

This example describes the stability results obtained in a terlipressin formulation screening study. This example contains results up to the 12 month time point at 25° C. and 30° C. and will continue up to 3 years. The purpose of this study was to investigate the impact of pH, sodium sulfate and sodium acetate buffer in a $2^3$ full factor design of experiments ("DoE") with 2 center points (CP):

pH: 4.6-5.4

Sodium sulfate: 0-80 mM

Sodium acetate: 1-9 mM

The reference formulation used in the study corresponds to the commercial terlipressin formulation GLYPRESSIN®: pH 3.7, 20 mM sodium acetate, 9 mg/mL NaCl. The table below shows the compositions of the formulations tested in this example.

TABLE 4

| Formulation | Terlipressin [mg/mL] | pH[1] | Stabilizer | Buffer [mM][2] |
|---|---|---|---|---|
| 1A | 0.1 mg/mL | 4.6 | 80 mM sodium sulfate | 9 mM sodium acetate |
| 2A | 0.1 mg/mL | 5.0 | 40 mM sodium sulfate | 5 mM sodium acetate |
| 3A | 0.1 mg/mL | 4.6 | 0 mM sodium sulfate | 9 mM sodium acetate |
| 4A | 0.1 mg/mL | 5.4 | 0 mM sodium sulfate | 9 mM sodium acetate |
| 5A | 0.1 mg/mL | 5.0 | 40 mM sodium sulfate | 5 mM sodium acetate |
| 6A | 0.1 mg/mL | 5.4 | 80 mM sodium sulfate | 9 mM sodium acetate |
| 7A | 0.1 mg/mL | 4.6 | 0 mM sodium sulfate | 1 mM sodium acetate |
| 8A | 0.1 mg/mL | 4.6 | 80 mM sodium sulfate | 1 mM sodium acetate |
| 9A | 0.1 mg/mL | 5.4 | 80 mM sodium sulfate | 1 mM sodium acetate |
| 10A | 0.1 mg/mL | 5.4 | 0 mM sodium sulfate | 1 mM sodium acetate |
| 11A[3] | 0.1 mg/mL | 5.0 | 0 mM sodium sulfate | 0 mM sodium acetate |
| 12A[3] | 0.1 mg/mL | 5.0 | 40 mM sodium sulfate | 0 mM sodium acetate |
| 13A[3] | 0.1 mg/mL | 5.0 | 80 mM sodium sulfate | 0 mM sodium acetate |
| 14A | 0.1 mg/mL | 3.7 | 9 mg/mL NaCl | 20 mM sodium acetate |

[1]pH was adjusted with 0.2M NaOH or 0.1N $H_2SO_4$. Formulation 14A was adjusted with 0.2M NaOH or 0.2M acetic acid.
[2]Terlipressin acetate contributed approximately 0.2 mM which is included in the sodium acetate concentration.
[3]These formulations showed high interferences from leachables and were not evaluated Storage Conditions The formulation screening samples were stored at:
- 25° C./60% R.H for two years (may be further extended to 3 years); sampling intervals at 0 months, 1 month, 3 months, 6 months, 9 months, 12 months, 18 months, and 24 months
- 30° C./75% R.H for up to two years (may be further extended to 3 years); 0 months, 1 month, 3 months, 6 months, 9 months, 12 months, 18 months, and 24 months The vials were stored vertically to avoid the contact between the formulations and rubber stoppers.

The acceptance criteria used to assay the stability of the formulations is provided in the below table. The limit for each impurity was initially set at the qualification limit for impurities in synthetic peptides according to the European Pharmacopeia, Substances for Pharmaceutical Use, Table 2034.-2. The limit for individual unidentified impurities corresponds to the identification limit according the European Pharmacopeia.

TABLE 7

| Test | Test procedure | Tentative acceptance criteria |
|---|---|---|
| Appearance | | |
| Clarity of solution | Visual inspection | Clear solution |
| Colouration of solution | Visual inspection | Colourless solution |
| Assay | | |
| Content of terlipressin free base | UPLC | 0.094-0.106 mg/mL and as high as possible |
| Degradation products | | |
| Sum of degradation products | UPLC | ≤3.5% and as small as possible |
| desGly[1], Gly[2], Gly[3]-terlipressin | UPLC | ≤0.1% and as small as possible |
| desGly[1], Gly[2]-terlipressin | UPLC | ≤1.0%* and as small as possible |
| desGly[1]-terlipressin | UPLC | ≤1.0%* and as small as possible |
| [Gly[12]OH]terlipressin | UPLC | ≤1.0%* and as small as possible |
| [Asp[8]]terlipressin | UPLC | ≤1.0%* and as small as possible |
| [Glu[7]]terlipressin | UPLC | ≤1.0%* and as small as possible |
| [Ac-Gly[1]]terlipressin | UPLC | ≤1.0%* and as small as possible |
| Any individual terlipressin dimer | UPLC | ≤1.0%* and as small as possible |
| Any individual unknown impurity | UPLC | <0.5%* and as small as possible |
| General tests | | |
| pH of solution | Ph. Eur. Curr. Ed. | 4.5 to 6 maintained at target ≤± 0.32 |

*Limits for impurities according to European Pharmacopeia, Substances for Pharmaceutical Use, Table 2034.-2

The following reverse phase UPLC method was used to assay terlipressin content and impurities in terlipressin solutions (0.1 mg/mL). The analysis was performed on a C18 column (Phenomenex Luna Omega $C_{18}$, 1.6 µm, 2.1×150 mm) with gradient elution at 60° C. and UV detection at 210 nm by using a Waters Acquity or equivalent LC system. The below table shows the parameters of the UPLC method.

TABLE B

| Mobile phase A: 0.1M ammonium phosphate buffer pH 3.0 Mobile phase B: 40% (v/v) acetonitrile, 60% (v/v) mobile phase A Flow: 0.4 ml/min Injection volume: 10 µl | | |
|---|---|---|
| Gradient | % A | % B |
| Initial | 80 | 20 |
| 10 min | 70 | 30 |
| 20 min | 0 | 100 |
| 21 min | 80 | 20 |
| 25 min | 80 | 20 |

Figure 4:
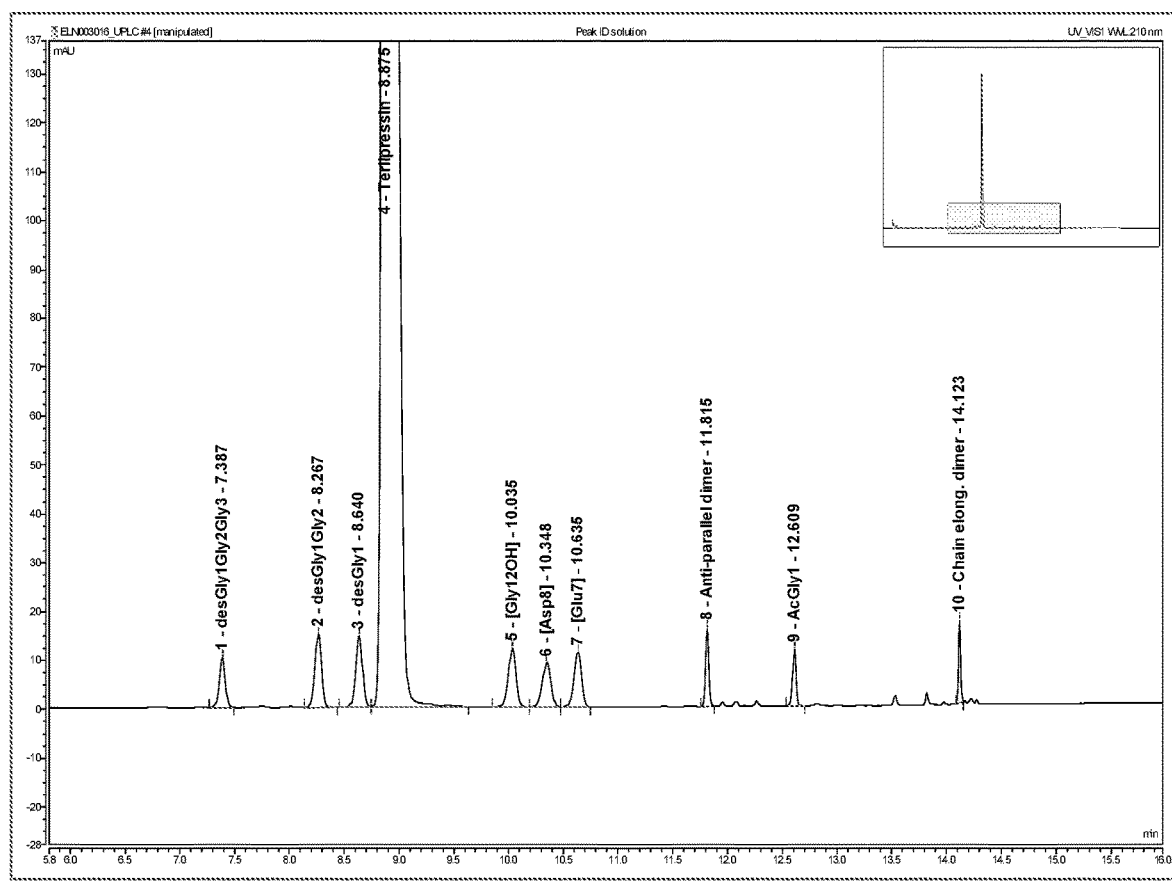
FIG. 4 shows a chromatogram of terlipressin and specific terlipressin-related impurities described herein.

FIG. 4 shows a chromatogram of terlipressin and specific terlipressin-related impurities described herein. Terlipressin content was determined against an external one-point calibration curve and the impurities were evaluated as area% of the total peak area. Peaks with a relative peak area of <0.05% were not reported or included in the sum of impurities.

Results

The data from the 12 month timepoint at 30° C./75% RH was entered into MINITAB software (Minitab, LLC, State College, PA). The evaluation showed that the two stability limiting parameters were the sum of impurities and the amount of the desGly1Gly2-impurity. These two parameters were selected for further evaluation as shown in FIG. 4. The statistical evaluation of the data at 25° C./60% RH was very similar and is not shown herein.

From the statistical analysis, the most stable formulation was predicted to be the formulation with the lowest pH (4.6), the lowest amount of acetate buffer (1 mM) and the lowest amount of sodium sulfate (0 mM). Sodium sulfate was found to have a positive effect on the formation of the desGly1Gly2-impurity, but a negative effect on the sum of impurities.

The tables below summarize the sum of impurities obtained at the up to 12 month time point for formulations tested at 25° C./60% R.H and 30° C./75% R.H, respectively.

TABLE 8

| | Sum of Impurities for 25° C./60% R.H | | | | | | |
|---|---|---|---|---|---|---|---|
| Formulation | 0 M | 1 M | 2 M | 3 M | 6 M | 9 M | 12 M |
| 1A | 0.36 | 0.61 | 0.76 | 0.88 | 1.39 | 1.82 | 2.31 |
| 2A | 0.35 | 0.49 | 0.56 | 0.62 | 0.85 | 1.08 | 1.32 |
| 3A | 0.33 | 0.53 | 0.61 | 0.72 | 1.05 | 1.40 | 1.76 |
| 4A | 0.33 | 0.45 | 0.54 | 0.66 | 1.01 | 1.37 | 1.71 |
| 5A | 0.35 | 0.47 | 0.54 | 0.59 | 0.87 | 1.07 | 1.32 |
| 6A | 0.37 | 0.47 | 0.54 | 0.57 | 0.87 | 1.15 | 1.44 |
| 7A | 0.30 | 0.43 | 0.47 | 0.55 | 0.78 | 0.95 | 1.18 |
| 8A | 0.34 | 0.52 | 0.67 | 0.73 | 1.08 | 1.38 | 1.70 |
| 9A | 0.34 | 0.45 | 0.50 | 0.59 | 0.96 | 1.06 | 1.28 |
| 10A | 0.29 | 0.45 | 0.54 | 0.64 | 1.22 | 1.61 | 2.13 |
| 14A | 0.33 | 1.03 | 1.54 | 2.18 | 4.05 | 5.72 | 7.58 |

TABLE 9

| | Sum of Impurities for 30° C./75% R.H | | | | | | |
|---|---|---|---|---|---|---|---|
| Formulation | 0 M | 1 M | 2 M | 3 M | 6 M | 9 M | 12 M |
| 1A | 0.36 | 0.71 | 1.02 | 1.32 | 2.25 | 3.16 | 4.13 |
| 2A | 0.35 | 0.54 | 0.69 | 0.84 | 1.35 | 1.88 | 2.51 |
| 3A | 0.33 | 0.61 | 0.84 | 1.04 | 1.75 | 2.34 | 3.05 |
| 4A | 0.33 | 0.59 | 0.85 | 1.11 | 1.85 | 2.65 | 3.46 |
| 5A | 0.35 | 0.53 | 0.70 | 0.86 | 1.35 | 1.88 | 2.47 |
| 6A | 0.37 | 0.55 | 0.74 | 0.96 | 1.54 | 2.18 | 2.96 |
| 7A | 0.30 | 0.50 | 0.64 | 0.76 | 1.25 | 1.49 | 1.98 |
| 8A | 0.34 | 0.64 | 0.86 | 1.07 | 1.72 | 2.31 | 2.93 |
| 9A | 0.34 | 0.56 | 0.76 | 0.99 | 1.67 | 2.20 | 3.50 |
| 10A | 0.29 | 0.63 | 0.87 | 1.14 | 2.19 | 3.78 | 5.82 |
| 14A | 0.33 | 1.60 | 2.60 | 3.76 | 7.18 | 10.06 | 13.77 |

The results after 12 months show that a large improvement in stability at room temperature has been achieved, compared to the reference formulation. The stability data shown above indicate that the most stable formulation of the study is Formulation 7A, which contains no sodium sulphate, 1 mM acetate buffer, and is at pH 4.6.

The tables below summarize the stability data obtained at up to the 12 month time for Formula 7A.

TABLE 10

| | Formulation 7A Results, 25° C./60% R.H | | | | | | | | |
|---|---|---|---|---|---|---|---|---|---|
| Analysis | 0 M | 1 M | 2 M | 3 M | 6 M | 9 M | 12 M | 18 M | 24 M |
| Appearance of solution | OK | OK | OK | OK | OK | OK | OK | X | X |
| pH | 4.69 | 4.54 | 4.52 | 4.70 | 4.72 | 4.69 | 4.83 | X | X |
| Content of terlipressin (µg/mL) | 99.7 | NA | NA | NA | NA | NA | 99.9 | X | X |
| Sum of impurities | 0.30 | 0.43 | 0.47 | 0.55 | 0.78 | 0.95 | 1.18 | X | X |
| desGly1Gly2Gly3 | ND | ND | ND | ND | ND | ND | ND | X | X |
| desGly1Gly2 | 0.03 | 0.06 | 0.08 | 0.10 | 0.15 | 0.22 | 0.29 | X | X |
| desGly1 | 0.17 | 0.16 | 0.16 | 0.17 | 0.18 | 0.22 | 0.25 | X | X |
| [Gly12OH] | ND | 0.06 | 0.06 | 0.09 | 0.17 | 0.20 | 0.24 | X | X |
| [Asp8] | ND | 0.02 | 0.02 | 0.02 | 0.04 | 0.04 | 0.05 | X | X |
| [Glu7] | ND | 0.03 | 0.04 | 0.07 | 0.13 | 0.16 | 0.18 | X | X |
| [AcGly1] | 0.10 | 0.10 | 0.10 | 0.10 | 0.11 | 0.10 | 0.10 | X | X |
| Any terlipressin dimer | ND | ND | 0.01 | ND | 0.01 | 0.01 | 0.01 | X | X |

TABLE 10-continued

| | Formulation 7A Results, 25° C./60% R.H | | | | | | | | |
|---|---|---|---|---|---|---|---|---|---|
| Analysis | 0 M | 1 M | 2 M | 3 M | 6 M | 9 M | 12 M | 18 M | 24 M |
| Largest unknown (≥0.05%) | ND | ND | ND | ND | ND | ND | 0.05 | X | X |

NA = Not analysed
ND = Not detected
X = Timepoint not reached

TABLE 11

| | Formulation 7A Results, 30° C./75% R.H | | | | | | | | |
|---|---|---|---|---|---|---|---|---|---|
| Analysis | 0 M | 1 M | 2 M | 3 M | 6 M | 9 M | 12 M | 18 M | 24 M |
| Appearance of solution | OK | OK | OK | OK | OK | OK | OK | X | X |
| pH | 4.69 | 4.43 | 4.52 | 4.62 | 4.76 | 4.69 | 4.83 | X | X |
| Content of terlipressin (μg/mL) | 99.7 | NA | NA | NA | NA | NA | 98.5 | X | X |
| Sum of impurities | 0.30 | 0.50 | 0.64 | 0.76 | 1.25 | 1.49 | 1.98 | X | X |
| desGly1Gly2Gly3 | ND | ND | ND | ND | ND | ND | ND | X | X |
| desGly1Gly2 | 0.03 | 0.09 | 0.12 | 0.16 | 0.29 | 0.42 | 0.56 | X | X |
| desGly1 | 0.17 | 0.17 | 0.19 | 0.20 | 0.25 | 0.33 | 0.39 | X | X |
| [Gly12OH] | ND | 0.07 | 0.13 | 0.15 | 0.24 | 0.29 | 0.36 | X | X |
| [Asp8] | ND | 0.02 | 0.02 | 0.04 | 0.05 | 0.06 | 0.09 | X | X |
| [Glu7] | ND | 0.05 | 0.08 | 0.12 | 0.19 | 0.23 | 0.31 | X | X |
| [AcGly1] | 0.10 | 0.10 | 0.10 | 0.10 | 0.11 | 0.10 | 0.10 | X | X |
| Any terlipressin dimer | ND | 0.01 | 0.01 | ND | 0.01 | 0.01 | 0.01 | X | X |
| Largest unknown (≥0.05%) | ND | ND | ND | ND | 0.05 | 0.06 | 0.07 | X | X |

NA = Not analysed
ND = Not detected
X = Timepoint not reached

Extrapolation of Stability Data

Figure 5:
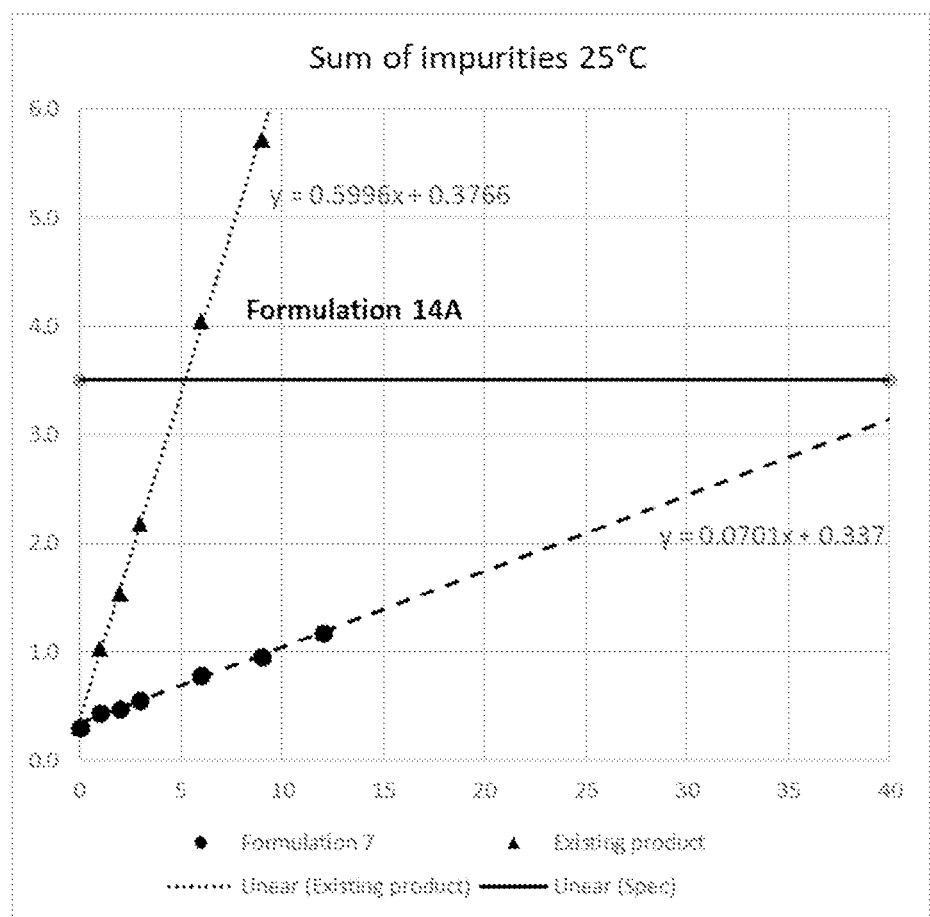
FIG. 5 is a graphical depiction of the extrapolation of sum of impurities data at 25° C./60% RH of Formulation 7A and Formulation 14A (reference formulation).
Figure 6:
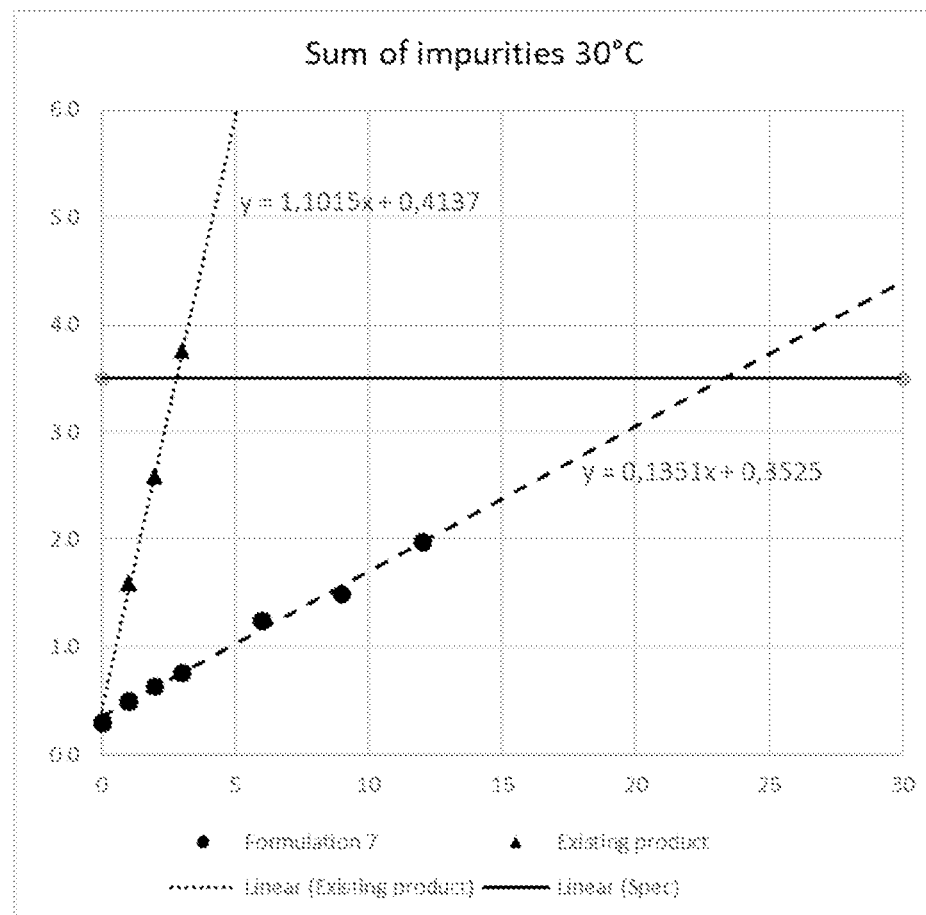
FIG. 6 is a graphical depiction of the extrapolation of sum of impurities data at 30° C./75% RH of Formulation 7A and Formulation 14A (reference formulation).

FIGS. 5 and 6 show the extrapolation of sum of impurities data at 25° C./60% RH and 30° C./75% RH of Formulation 7A and Formulation 14A (reference formulation). The extrapolation predicts that Formulation 7A will stay within specification (≤3.5% impurities) with a good margin for 36 months at 25° C./60% RH. It can be noted that the reference formulation (Formulation 14A) exceeded the specification limit already after about 5 months at 25° C./60% RH.

Despite the small difference in temperature, the data at 30° C./75% RH is very different. At 30° C., Formulation 7A is predicted to exceed the specification for sum of impurities after about 24 months without any margin at all. This indicates that Formulation 7A is most likely not a suitable formulation for climate zone III/IV with the suggested specification.

Figure 7:
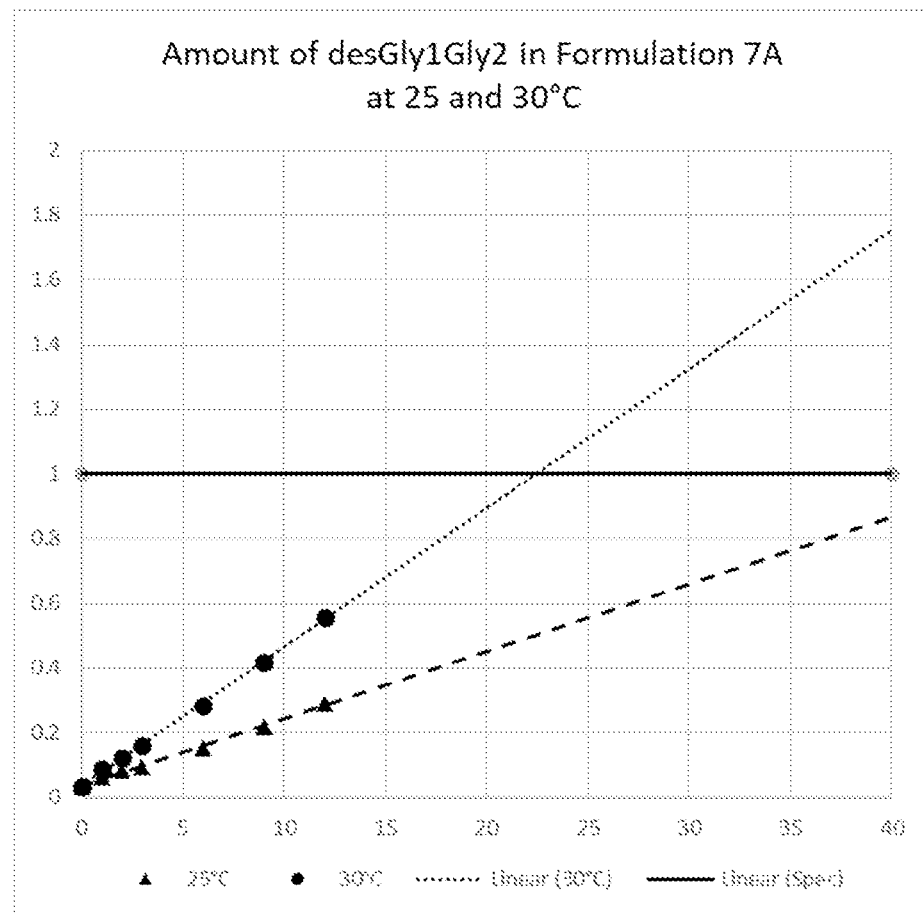
FIG. 7 is a graphical depiction of the extrapolation of desGly1Gly2-data at 25° C./60% RH and 30° C./75% RH of Formulation 7A.

However, the improvement in stability compared to the existing product is remarkable at both temperatures. By dividing the slopes of the regression lines of existing product and Formulation 7A, the following factors of improvement can be estimated:

25° C./60% RH: 0.5996/0.0701=8.6 times improvement
30° C./75% RH: 1.1015/0.1351=8.2 times improvement The second potentially stability limiting parameter is the amount of desGly1Gly2, which is the result of the diketopiperazine reaction. FIG. 7 shows the extrapolation of desGly1Gly2-data at 25° C./60% RH and 30° C./75% RH of Formulation 7A. The extrapolation predicts that Formulation 7A will stay within specification (≤1.0%) with a good margin for 36 months at 25° C./60% RH. At 30° C./75% RH, Formulation 7A is predicted to exceed the specification for sum of impurities after about 23 months.

Example 6

This example describes stability results obtained in a terlipressin formulation screening study performed in a similar manner as described in Example 5.

Tested Formulations

The table below shows the compositions of the formulations tested in this example and the corresponding sum of impurities obtained after 1 and 3 months of storage at 40° C.

TABLE 12

| Formulation | Terlipressin* [mg/mL] | pH | Isotonic Agent [mg/mL] | Total Acetate Conc* [mM] | Sum of impurities after 1 month at 40° C./75% RH | Sum of impurities after 3 months at 40° C./75% RH |
|---|---|---|---|---|---|---|
| 1B | 0.1 mg/mL | 4.6 | 4.5 NaCl | 0.8 | 0.92 | 2.02 |
| 2B | 0.1 mg/mL | 4.2 | 9.0 NaCl | 0.4 | 1.54 | 3.75 |
| 3B | 0.1 mg/mL | 4.2 | 0.0 NaCl | 0.4 | 0.94 | 1.93 |

TABLE 12-continued

| Formulation | Terlipressin* [mg/mL] | pH | Isotonic Agent [mg/mL] | Total Acetate Conc* [mM] | Sum of impurities after 1 month at 40° C./75% RH | Sum of impurities after 3 months at 40° C./75% RH |
|---|---|---|---|---|---|---|
| 4B | 0.1 mg/mL | 5.0 | 0.0 NaCl | 0.4 | 0.83 | 1.80 |
| 5B | 0.1 mg/mL | 5.0 | 0.0 NaCl | 1.2 | 0.87 | 1.91 |
| 6B | 0.1 mg/mL | 4.6 | 4.5 NaCl | 0.8 | 0.92 | 1.91 |
| 7B | 0.1 mg/mL | 5.0 | 9.0 NaCl | 1.2 | 0.80 | 1.60 |
| 8B | 0.1 mg/mL | 5.0 | 9.0 NaCl | 0.4 | 0.78 | 1.54 |
| 9B | 0.1 mg/mL | 4.2 | 9.0 NaCl | 1.2 | 1.49 | 3.51 |
| 10B | 0.1 mg/mL | 4.2 | 0.0 NaCl | 1.2 | 0.95 | 1.92 |
| 11B | 0.1 mg/mL | 5.0 | 50 Mannitol | 1.2 | 0.90 | 1.90 |
| 12B | 0.1 mg/mL | 4.2 | 0.0 NaCl | 0.4 | 0.88 | 1.61 |
| 13B | 0.6 mg/mL | 4.6 | 0.0 NaCl | 1.2 | 0.76 | 1.60 |
| 14B | 4.0 mg/mL | 4.6 | 0.0 NaCl | 8.3 | 1.06 | 2.52 |

*Terlipressin provided as terlipressin acetate
*Acetate added as sodium acetate; total concentration includes amount contributed by terlipressin acetate The results show that a lower acetate concentration is associated with improved stability. For example, Formulations 7B and 8B are identical except that Formulation 8B has less acetate, and is more stable. The results also show that including NaCl improves stability. For example, Formulations 4B and 8B are identical except that Formulation 8B has NaCl, and is more stable.

What is claimed is:

1. A pharmaceutical composition comprising terlipressin or a pharmaceutically acceptable salt thereof, a monovalent organic buffer salt comprising an acetate buffer salt in an amount that provides a total buffer concentration in the composition of 5 mM or less, and water, wherein the pharmaceutical composition has a pH of from about 4.5 to about 6.

2. The pharmaceutical composition of claim 1, further comprising sodium chloride (NaCl).

3. The pharmaceutical composition of claim 1, further comprising mannitol.

4. The pharmaceutical composition claim 1, wherein the composition has a pH of about 4.8+0.3.

5. The pharmaceutical composition of claim 1, wherein the acetate buffer salt is selected from one or more of sodium acetate, ammonium acetate, and potassium acetate.

6. The pharmaceutical composition of claim 1, wherein the buffer salt is present in an amount to provide a total buffer concentration from about 0.1 mM to about 5 mM.

7. The pharmaceutical composition of claim 2, comprising sodium chloride at a concentration from about 1 mg/mL to about 10 mg/mL.

8. The pharmaceutical composition of claim 1, comprising mannitol at a concentration from about 30 mg/mL to about 70 mg/mL.

9. The pharmaceutical composition of claim 1, comprising terlipressin or pharmaceutically acceptable salt thereof in an amount to provide from about 0.1 mg/mL to about 5 mg/mL terlipressin free base.

10. The pharmaceutical composition of claim 1, comprising terlipressin acetate in an amount to provide from about 0.1 mg/mL to about 5 mg/mL terlipressin free base.

11. The pharmaceutical composition claim 1, comprising terlipressin acetate in an amount to provide from about 0.1 mg/mL to about 5 mg/mL terlipressin free base, sodium acetate in an amount to provide a total acetate concentration ranging from about 0.1 mM to about 5 mM, optionally, sodium chloride at a concentration ranging from about 1 mg/mL to about 10 mg/mL, and water.

12. The pharmaceutical composition of claim 1, consisting essentially of terlipressin acetate in an amount to provide from about 0.1 mg/mL to about 5 mg/mL terlipressin free base, sodium acetate in an amount to provide a total acetate concentration ranging from about 0.1 mM to about 5 mM, optionally, sodium chloride at a concentration ranging from about 1 mg/mL to about 10 mg/mL, and water.

13. The pharmaceutical composition of claim 1, wherein the pharmaceutical composition is selected from:

(a) a pharmaceutical composition comprising terlipressin acetate in an amount to provide 0.1 mg/mL terlipressin free base, sodium acetate in an amount to provide a total acetate concentration of about 1 mM, sodium chloride at a concentration of about 9 mg/mL, and water, wherein the composition has a pH of about 4.8±0.3;

(b) a pharmaceutical composition comprising terlipressin acetate in an amount to provide 1 mg/mL terlipressin free base, sodium acetate in an amount to provide a total acetate concentration of about 1 mM, sodium chloride at a concentration of about 9 mg/mL, and water, wherein the composition has a pH of about 4.8±0.3;

(c) a pharmaceutical composition comprising terlipressin acetate in an amount to provide 2 mg/mL terlipressin free base, sodium acetate in an amount to provide a total acetate concentration of about 1 mM, sodium chloride at a concentration of about 9 mg/mL, and water, wherein the composition has a pH of about 4.8±0.3;

(d) a pharmaceutical composition comprising terlipressin acetate in an amount to provide 3 mg/mL terlipressin free base, sodium acetate in an amount to provide a total acetate concentration of about 1 mM, sodium chloride at a concentration of about 9 mg/mL, and water, wherein the composition has a pH of about 4.8±0.3;

(e) a pharmaceutical composition comprising terlipressin acetate in an amount to provide 4 mg/mL terlipressin free base, sodium acetate in an amount to provide a total acetate concentration of about 1 mM, sodium chloride at a concentration of about 9 mg/mL, and water, wherein the composition has a pH of about 4.8±0.3; and (f) a pharmaceutical composition comprising terlipressin acetate in an amount to provide 5 mg/mL terlipressin free base, sodium acetate in an amount to provide a total acetate concentration of about 1 mM, sodium chloride at a concentration of about 9 mg/mL, and water, wherein the composition has a pH of about 4.8±0.3.

14. The pharmaceutical composition of claim 1, wherein the pharmaceutical composition is selected from:
   (a) a pharmaceutical composition comprising terlipressin acetate in an amount to provide 0.1 mg/mL terlipressin free base, sodium acetate in an amount to provide a total acetate concentration of about 1 mM, and water, wherein the composition has a pH of about 4.8±0.3;
   (b) a pharmaceutical composition comprising terlipressin acetate in an amount to provide 1 mg/mL terlipressin free base, sodium acetate in an amount to provide a total acetate concentration of about 1 mM, and water, wherein the composition has a pH of about 4.8±0.3;
   (c) a pharmaceutical composition comprising terlipressin acetate in an amount to provide 2 mg/mL terlipressin free base, sodium acetate in an amount to provide a total acetate concentration of about 1 mM, and water, wherein the composition has a pH of about 4.8±0.3;
   (d) a pharmaceutical composition comprising terlipressin acetate in an amount to provide 3 mg/mL terlipressin free base, sodium acetate in an amount to provide a total acetate concentration of about 1 mM, and water, wherein the composition has a pH of about 4.8±0.3;
   (e) a pharmaceutical composition comprising terlipressin acetate in an amount to provide 4 mg/mL terlipressin free base, sodium acetate in an amount to provide a total acetate concentration of about 1 mM, and water, wherein the composition has a pH of about 4.8±0.3; and
   (f) a pharmaceutical composition comprising terlipressin acetate in an amount to provide 5 mg/mL terlipressin free base, sodium acetate in an amount to provide a total acetate concentration of about 1 mM, and water, wherein the composition has a pH of about 4.8±0.3.

15. The pharmaceutical composition of claim 1, wherein the pharmaceutical composition is stable at room temperature for at least 1 year.

16. The pharmaceutical composition of claim 1, wherein the pharmaceutical composition exhibits a stability such that one or more of:
   (a) after being stored at 25° C. and 60% relative humidity for a period of time of at least one year, the total impurity content in the composition is less than about 1.9% w/w based on the total weight of the terlipressin;
   (b) after being stored at 25° C. and 60% relative humidity for a period of time of 12 months, the total impurity content in the composition is less than about 1.9% w/w based on the total weight of the terlipressin;
   (c) after being stored at 25° C. and 60% relative humidity for a period of time of 18 months, the total impurity content in the composition is less than about 1.9% w/w based on the total weight of the terlipressin;
   (d) after being stored at 25° C. and 60% relative humidity for a period of time of 24 months, the total impurity content in the composition is less than about 1.9% w/w based on the total weight of the terlipressin; and
   (e) after being stored at 25° C. and 60% relative humidity for a period of time of 36 months, the total impurity content in the composition is less than about 1.9% w/w based on the total weight of the terlipressin.

\* \* \* \* \*